(12) United States Patent
Holm et al.

(10) Patent No.: US 7,176,282 B1
(45) Date of Patent: Feb. 13, 2007

(54) SOLID-PHASE PEPTIDE SYNTHESIS AND AGENT FOR USE IN SUCH SYNTHESIS

(75) Inventors: Arne Holm, Skodsborg (DK); Bjarne Due Larsen, Roskilde (DK)

(73) Assignee: Zealand Pharma A/S, Glostrup (DK)

( * ) Notice: Subject to any disclaimer, the term of this patent is extended or adjusted under 35 U.S.C. 154(b) by 0 days.

(21) Appl. No.: 09/551,336

(22) Filed: Apr. 18, 2000

Related U.S. Application Data

(63) Continuation-in-part of application No. 09/254,523, filed on Mar. 8, 1999, now abandoned.

(30) Foreign Application Priority Data

Sep. 9, 1996 (DK) .................................. 0971/96

(51) Int. Cl.
*A61K 38/00* (2006.01)
(52) U.S. Cl. ..................................................... 530/334
(58) Field of Classification Search ................ 530/334
See application file for complete search history.

(56) References Cited

U.S. PATENT DOCUMENTS 5,021,550 A 6/1991 Zeiger .................... 530/344

OTHER PUBLICATIONS

Larsen et al., 1994, Int. J. Peptide Protein Res. 43:1-9.
Medal et al, 1993, Int J. Peptide Protein Res. 41:250-260.
Larsen et al, 1993, J. Am. Chem. Soc. 115:6247-6253.
Kent, 1988, Ann. Rev. Biochem. 57:957-89.
Cameron et al, 1987, J. Chem. Soc., Chem. Commun. 270-272.
Chou et al, 1978, Ann. Rev. Biochem. 47:251-76.
W. E. Rapp, et al., "Prediction and prevention of peptide conformations during synthesis" Peptides, Chemistry, Structure and Biology, pp. 40-43 (1994).
Bruce Merrifield, "Solid Phase Synthesis", Science 232:341-347 (1986).

*Primary Examiner*—Bruce R. Campell
*Assistant Examiner*—Maury Audet
(74) *Attorney, Agent, or Firm*—Clark & Elbing LLP; Kristina Bieker-Brady

(57) ABSTRACT

The present invention relates to an improved process for the production of peptides by solid-phase synthesis. The invention also relates to agents, which are useful in solid-phase peptide synthesis.

10 Claims, 12 Drawing Sheets

A.

B.

SOLID-PHASE PEPTIDE SYNTHESIS AND AGENT FOR USE IN SUCH SYNTHESIS

This application is a continuation-in-part of U.S. patent application Ser. No. 09/254,523, filed Mar. 8, 1999, now abandoned, which is a continuation of PCT/DK97/00375, the contents of which are herein incorporated by reference.

FIELD OF THE INVENTION

The present invention relates to an improved process for the production of peptides by solid-phase synthesis. The invention also relates to agents, which are useful in solid-phase peptide synthesis.

BACKGROUND OF THE INVENTION

Solid-phase peptide synthesis (SPPS) is a highly successful method introduced by Merrifield in 1963 (Merrifield, R. B. (1963) J. Amer. Chem. Soc. 85, 2149–2154). Numerous peptides have been synthesized with this technique since then. Methods used in the prior art to chemically synthesize peptides and proteins are reviewed in Kent, S. B. H. (1988), Ann. Rev. Biochem. 57, 957–989.

Two strategies for the assembly of peptide chains by solid-phase synthesis have been used, viz. the stepwise solid-phase synthesis, and solid-phase fragment condensation. In stepwise SPPS, the C-terminal amino acid in the form of an N-$\alpha$-protected, if necessary, side-chain, protected reactive derivative is covalently coupled either directly or by means of a suitable linker to a "solid"-support, e.g., a polymeric resin, which is swollen in an organic solvent. The N-$\alpha$-protective group is removed, and the subsequent protected amino acids are added in a stepwise fashion. When the desired peptide chain length has been obtained, the side-chain protective groups are removed, and the peptide is cleaved from the resin This may be done in separate steps or at the same time. In solid-phase fragment condensation, the target sequence is assembled by consecutive condensation of fragments on a solid support using protected fragments prepared by stepwise SPPS.

Over the years, two coupling strategies have been developed based on the use of different N-$\alpha$-protective groups and matching side-chain protective groups. Merrifield used tert.butyloxycarbonyl (Boc) as the N-$\alpha$ protective group, while 9-fluorenylmethyloxycarbonyl (Fmoc) was introduced by Carpino and Han (Carpino, L. A. and Hari, G. Y. (1972), J. Org. Chem. 37, 3404–3409). The operations involved in one cycle of chain extension in stepwise SPPC using Boc- and Fmoc-chemistries are illustrated in FIG. 1 (taken from Kent, S. B. H. (1988), Ann. Rev. Biochem. 57, 957–989). The side-chain protection in both cases was tert.butyl, trityl and arylsulfonyl based, and these side chains were deprotected with TFA.

The N-$\alpha$-Boc-protected peptide coupled to a PAM-resin was N-$\alpha$-deprotected with trifluoroacetic acid (TFA). The resulting amine salt was washed and neutralized with a tertiary amine. The subsequent peptide bond was formed by reaction with an activated Boc-amino acid, e.g., a symmetric anhydride. Generally, the side-chain protection is benzyl-based, and the deprotection is made with HF or a sulphonic acid.

The N-$\alpha$-Fmoc protected peptide coupled to a resin was N-$\alpha$-deprotected by treatment with a secondary amine, normally piperidine, in an organic solvent, e.g., N,N-dimethyl formamide (DMF) or dichloromethane (DCM). After washing, the neutral peptide resin was reacted with an activated Fmoc-amino acid, e.g., a hydroxybenzotriazole active ester.

While the Boc- and Fmoc-strategies have been used for essentially all current practical peptide synthesis, other N-$\alpha$protective groups have been proposed (Stewart, J. M. and Young, J. D., Solid phase peptide synthesis, Pierce Chemical Company (1984)). Boc forms an acid-labile urethane group, and other proposals of this category have been biphenylisopropyloxycarbonyl (Bpoc), 3,5-dimethoxyphenylisopropyloxycarbonyl (Ddz), phenylisopropyloxycarbonyl (Poc) and 2,3,5-tetramethylbenzyloxycarboxyl (Tmz). Other types of N-$\alpha$ protecting groups available include nitrophenylsulfenyl (Nps) which can be removed by either very dilute anhydrous acid, e.g. HCl, or by nucleophilic attack, e.g. with methyl-3-nitro-4-mercapto benzoate. Also dithiasuccinyl (Dts), which is removable by nucleophilic attack, might be used.

SPPS has the general advantage that it lends itself to fully automated or semi-automated chain assembly chemistry. A system for SPPS under low pressure continuous flow conditions was developed by Dryland & Sheppard (1986) J. Chem. Soc. Perkin Trans. I, 125–137 and was further refined (Cameron, L., Meldal, M. and Sheppard, R. C (1987), J. Chem. Soc. Chem. Commun. 270–272 and Meldal, M., Bisgaard Holm, C., Boejesen, G., Havsteen Jakobsen, M. and Holm, A. (1993), Int. J. Peptide and Protein Res. 41, 250–260 and WO 90/02605). While SPPS has now developed to be a cornerstone in protein and peptide synthesis, certain problems still remain to be solved. Since some of these problems might well be related to the peptide structure, a brief discussion regarding protein conformation is deemed proper.

Empirical predictions of protein conformations have been made by Chou & Fasman (Chou, P. Y. and Fasman, G. D. (1978), Ann. Rev. Biochem. 47, 251–276.). It is well-known that protein architectures may be described in terms of primary, secondary, tertiary and quaternary structure. The primary structure refers to the amino acid sequence of the protein. The secondary structure is the local spatial organization of the polymer backbone without consideration of the side-chain conformation. As examples of secondary structures, $\alpha$-helixes, $\beta$-sheets and $\beta$-turns, which are chain reversal regions consisting of tetrapeptides can be mentioned. The tertiary structure is the arrangement of all the atoms in space, including disulphide bridges and side-chain positions, so that all short and long-range interactions are considered. The term quaternary structure may be used to denote the interaction between subunits of the protein, e.g. the $\alpha$ and $\beta$-chains of hemoglobins.

Following a discussion of earlier attempts to correlate protein secondary structure with amino acid compositions, where e.g., Ser, Thr, Val, Ile and Cys were classified as "helix breakers" and Ala, Leu and Glu as "helix formers", while hydrophobic residues were classified as strong "$\beta$-formers", and proline together with charged amino acid residues as "$\beta$-breakers", Chou & Fasman made a statistical analysis of 29 proteins with known X-ray structure in order to establish prediction rules for $\alpha$- and $\beta$-regions (Chou and Fasman, 1978, Ann. Rev. Biochem. 47:251–276). Based on these studies, they determined so-called propensity factors P$\alpha$, P$\beta$ and Pt which are conformational parameters expressing the positional preferences as $\alpha$-helix, $\beta$-sheet and $\beta$-turn, respectively, for the natural L-amino acids forming part of proteins. For the sake of convenience, the P$\alpha$ and P$\beta$ values are listed below in Table 1. Generally speaking, values below 1.00 indicate that the amino acid in question must be regarded as unfavourable for the particular secondary structure. As an example, the hydrophobic acids (e.g. Val, Ile, Leu) are strong β-sheet formers, while the charged amino acids (e.g. Glu, Asp, His) are β-sheet breakers.

TABLE I

PROPENSITY VALUES

| Pα  |      | Pβ  |      |
|-----|------|-----|------|
| Glu | 1.51 | Val | 1.70 |
| Met | 1.45 | Ile | 1.60 |
| Ala | 1.42 | Tyr | 1.47 |
| Leu | 1.21 | Phe | 1.38 |
| Lys | 1.16 | Trp | 1.37 |
| Phe | 1.13 | Leu | 1.30 |
| Gln | 1.11 | Cyr | 1.19 |
| Trp | 1.08 | Thr | 1.19 |
| Ile | 1.08 | Gln | 1.10 |
| Val | 1.06 | Met | 1.05 |
| Asp | 1.01 | Arg | 0.93 |
| His | 1.00 | Asn | 0.89 |
| Arg | 0.98 | His | 0.87 |
| Thr | 0.83 | Ala | 0.83 |
| Ser | 0.77 | Ser | 0.75 |
| Cys | 0.70 | Gly | 0.75 |
| Tyr | 0.69 | Lys | 0.74 |
| Asn | 0.67 | Pro | 0.55 |
| Pro | 0.57 | Asp | 0.54 |
| Gly | 0.57 | Glu | 0.37 |

In the α-helix structure, the spiral configuration of the peptide has been found to be held rigidly in place by hydrogen bonds between the hydrogen atom attached to the nitrogen atom in one repeating unit and the oxygen atom is attached to a carbon atom three units along the chain. If a polypeptide is brought into solution, the α-helix can be made to unwind to form a random coil, by adjustment of the pH. The transition from α-helix random coil occurs within a narrow pH. Since the hydrogen bonds are all equivalent in bond strength in the α-helix, they tend to let go all at once. The change can also be induced by heat.

The β-sheet structure consists of fully extended peptide chains in which hydrogen bonds link the hydrogen atoms on one chain to the oxygen atoms in the adjoining chain. Thus hydrogen bonds do not contribute to the internal organization of the chain as they do in the α-helix, but only bond chain to chain. Adjacent chains may be parallel or antiparallel. β-turns are frequently observed in these parts of a peptide chain which connect antiparallel chains in a β-sheet structure. In a β-turn, the CO- and NH-groups from amino acid No. n in the peptide chain form hydrogen bond to the corresponding groups in amino acid No. n+4.

α-helix and β-sheet constitute strongly varying parts of the peptide conformation of proteins (from 0 to 80%), and the remaining parts of the proteins are folded in other structures. In most proteins, sections of the peptide chains appear as irregularly folded "random coils".

Turning now to the general problems still prevailing in connection with SPPS, S. B. H. Kent (Kent, S. B. H. (1988), Ann. Rev. Biochem. 57, 957–989) highlights the synthesis of "difficult sequences". Obviously, the whole rationale of SPPS is based on a complete N-α-deprotection prior to each of the coupling steps involved. By the same token, ideally all of the N-α-deprotected amino groups should be coupled to the reactive amino acid derivative according to the desired sequence, i.e. a complete aminoacylation should take place. Kent states that the most serious potential problem in stepwise SPPS is incomplete peptide bond formation giving rise to peptides with one or more amino acids missing (deletions), but with properties similar to the target sequence. Such incomplete couplings are more prevalent in some sequences than in others, hence the term "difficult sequences", and are apparently also more predominant in Fmoc-chemistry than in Boc-chemistry.

A number of recognized "difficult sequences" have been previously studied. During SPPS of homo-oligopeptides containing leucine or alanine using the Fmoc-strategy, ineffective N-α-deprotection with piperidine in a sequence dependent manner (B. D. Larsen, C. Larsen, and A. Holm in Peptides 1990, E. Giralt and D. Andreu, (Eds). 1991 ESCOM Science Publishers B.V., p. 183–185; and Larsen, B. D., and Holm, A. (1994), Int. J. Peptide & Protein Res. 43,1–9.) was observed. Investigations showed that this phenomenon was associated with subsequent slow or incomplete amino acid coupling and evidence for β-sheet aggregation of the growing peptide chain was presented as a cause for the difficult couplings and incomplete Fmoc-deprotections. This evidence was based on general physical-chemical observations (Larsen, B. D., and Holm, A. (1994), Int. J. Peptide & Protein Res. 43, 1–9) and on a detailed Raman Near Infrared Spectroscopic study (Due Larsen, B., Christensen, D-H., Holm, A., Zillmer, R., and Faurskov, 0. (1993), J. Amer. Chem. Soc. 115, 6247–6253).

Kent (Kent, S. B. H. (1988), Ann Rev. Biochem. 57, 957–989) proposes a number of solutions to the problem related to sequence-dependent coupling difficulties, viz. the use of heat in the coupling step and a quantitative conversion of residual unreacted resin-bound peptide chains to terminated species in a "capping" procedure. However, at the present time, no procedure has been formulated for synthesizing these "difficult sequences" in high yield and purity.

OBJECTS OF THE INVENTION

It is therefore one object of the present invention to provide an improved SPPS according to which peptides which are recognized as or prove to be "difficult sequences", can be synthesized in high yield and purity. A further object of the invention is to provide an improved SPPS which provides for reduced coupling times, not only for difficult sequences, but also for otherwise uncomplicated sequences where it is desirable to reduce the normally long coupling times. A still further object of the invention is to provide an agent or a kit for use in SPPS, whereby the above-mentioned process improvements are obtained.

SUMMARY OF THE INVENTION

The invention is directed to a process for the production of a peptide having the structure

wherein AA is an L- or D-amino acid residue,

X is hydrogen or an amino protective group

Y is OH, NH$_2$ or an amino acid sequence comprising from 3 to 9 amino acid residues and n is an integer greater than 2 by solid phase synthesis comprising:

(a) coupling the C-terminal amino acid in the form of an N-alpha-protected reactive derivative to the support optionally by means of a linker, wherein said C-terminal amino acid comprises a presequence comprising from 3 to 9 amino acids and preferably from 5–7 amino acids independently selected from native L-amino acids having a side chain functionality which is protected during the coupling steps and having a propensity factor Pα>0.57 and a propensity factor Pβ≦1.10 or the corresponding D-amino acids;
(b) adding subsequent amino acids forming the peptide sequence by stepwise coupling or coupling as a peptide fragment in the form of protected fragments;
(c) removing the protecting groups from the peptide sequence of (b) and
(d) optionally cleaving the presequence from the formed peptide.

Furthermore, the invention is directed to agents that are useful in solid phase peptide synthesis. These include agents having the formulae

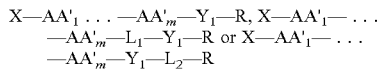

wherein R is a solid support applicable in solid phase peptide synthesis, $Y_1$ is an amino acid sequence comprising from 3 to 9, preferably from 5 to 7 amino acid residues independently selected from L-amino acids having a side chain functionality which is protected during the coupling steps and having a propensity factor Pα>0.57 and a propensity factor Pβ≦1.10, or the corresponding D-amino acid, AA' is an L or D-amino acid residue, $L_1$ is a linker wherein the $L_1$—AA'$_m$ bond is selectively cleaved, $L_2$ is a linker, wherein the $L_2$—R bond is selectively cleaved, m is zero or an integer from 1 to 40 and X is hydrogen or an amino protective group.

Alternatively, the agent may have the have the general formula

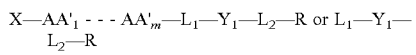

wherein R is a solid support applicable in solid phase peptide synthesis, $Y_1$ is an amino acid sequence comprising from 3 to 9, preferably from 5 to 7 amino acid residues independently selected from L-amino acids having a side chain functionality which is protected during the coupling steps and having a propensity factor Pα>0.57 and a propensity factor Pβ≦1.10 or the corresponding D-amino acid, AA' is an L or D-amino acid residue, m is zero or an integer from 1 to 40 and X is hydrogen or an amino protective group, $L_1$ is a linker wherein the $L_1$—AA'$_m$ and $L_2$ is a linker with orthogonal cleavage conditions relative to the first linker such that the $L_2$—R bond is selectively cleaved.

DETAILED DESCRIPTION OF THE INVENTION

Figure 1:
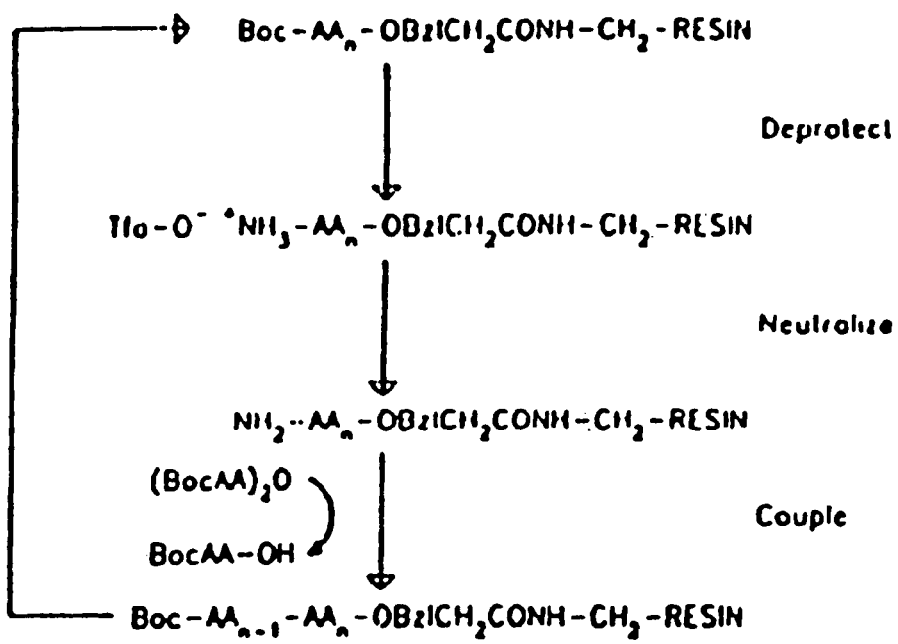
FIG. 1 shows the traditional synthetic scheme followed with Boc and Fmoc-protected amino acids.
Figure 1:
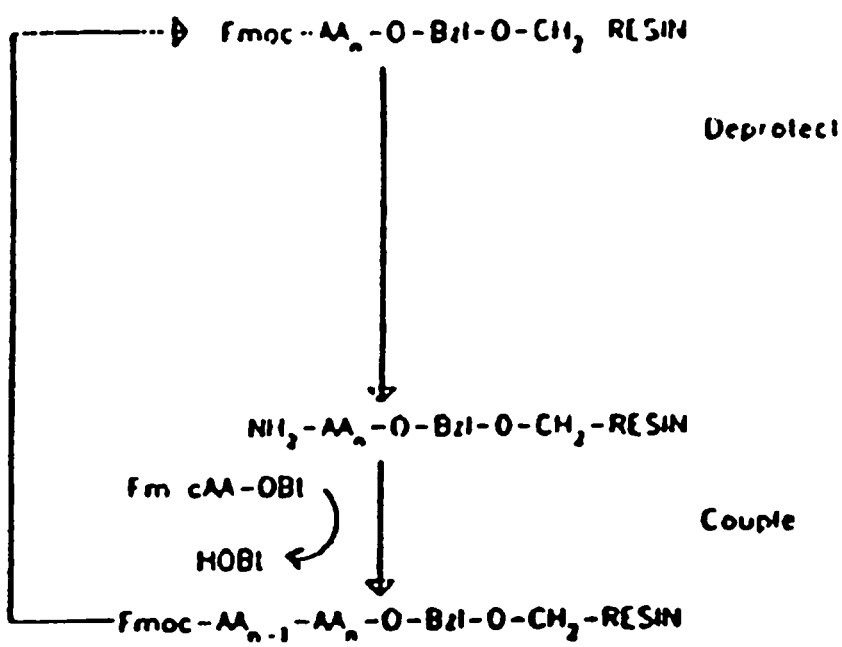

In contrast to prior art methods, the present invention is based on the incorporation of a particular presequence in the C-terminal portion of a peptide sequence attached to the solid support. This is a fundamental breach with the prior art attempts to deal with difficult sequences, where the focus was on the reaction conditions and the nature of the solid support. As further discussed below, the C-terminal sequence by which the desired peptide is attached to the solid support might also include suitable linkers in order to provide for e.g., better attachment or cleavage conditions.

Thus in a first aspect, the present invention relates to a process for the production of the peptide having the structure

wherein AA is an L- or D-amino acid residue,

X is hydrogen or an amino protective group

Y is OH, NH$_2$ or an amino acid sequence comprising from 3 to 9 amino acid residues and n is an integer greater than 2 by solid phase synthesis comprising:
(a) coupling the C-terminal amino acid in the form of an N-alpha-protected reactive derivative to the support optionally by means of a linker, wherein said C-terminal amino acid comprises a presequence comprising from 3 to 9 amino acids independently selected from native L-amino acids having a side chain functionality which is protected during the coupling steps and having a propensity factor Pα>0.57 and a propensity factor Pβ≦1.10 or the corresponding D-amino acids;
(b) adding subsequent amino acids forming the peptide sequence by stepwise coupling or coupling as a peptide fragment in the form of protected fragments;
(c) removing the protecting groups from the peptide sequence of (b);
(d) optionally cleaving the presequence from the formed peptide.

It will be understood that when X is OH, the product formed after cleavage will be a peptide AA$_1$—AA$_n$—OH, i.e. Y=OH, while in case of X being NH$_2$ a peptide amide AA$_1$—AA$_n$—NH$_2$ is formed, i.e. Y=NH$_2$. In a preferred embodiment, there are from 5–7 amino acids in the presequence. In a preferred embodiment, there are from 5–7 amino acids in the presequence.

L-amino acids meeting the above-mentioned limits for the propensity factors Pα and Pβ include but are not limited to Lys, Glu, Asp, Ser, His, Asn, Arg, Met and Gln. These amino acids all have a side chain functionality selected from a carboxy, carboxamido, amino, hydroxy, guanidino, sulphide or imidazole group. Presently preferred amino acids in the presequence are Lys and Glu and combinations thereof, e.g. $(Glu)_q(Lys)_p$, where p+q is 3 to 9, preferably 6 to 9, and the order of Lys and Glu is arbitrarily chosen.

The N-α amino group of the amino acids or peptide fragments used in each coupling step should be suitably protected during the coupling. The protective group may be Fmoc or Boc or any other suitable protective group, e.g., those described above with reference to Stewart, J. M. and Young, J. D., Solid phase peptide synthesis, Pierce Chemical Company (1984); and Peptides: Synthesis, structures and applications. Gutte, B., Ed. Academic Press Inc. 1995. It is important that the side chain functionality in the presequence is suitably protected during the coupling steps. Such protective groups are well-known to a person skilled in the art and may be selected from the group consisting of a carboxy, carboxamido, amino, hydroxy, guanidino, sulphide and imidazole moiety.

Without wishing to be bound by any particular theory, it is assumed that the physical-chemical properties of the protected side-chain of the presequence exemplified by lysine are responsible for the observed "structural assisted peptide synthesis" (SAPS) by reducing or eliminating β-sheet formation in the polyalanine sequence.

In accordance with the above observations, another aspect of the present invention relates to a method for the solid phase synthesis of peptides as described above having the further feature that a linker is inserted between the presequence attached to the support and the desired peptide sequence $AA_1$–$AA_n$, which enables a selective cleavage of said sequence. Preferably, the linker is optically active. An applicable group of linkers is α-hydroxy and α-amino acids of the general formula

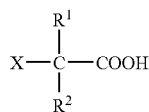

wherein X is OH or $NH_2$ and $R^1$ and $R^2$ are independently selected from H, $C_{1-3}$ alkyl, phenyl and substituted phenyl, where the substituents are one or more electron donating substituents chosen among $C_{1-3}$ alkoxy, $C_{1-3}$ alkyl, or two vicinal substituent groups are joined to form a 5 or 6 membered ring together with the carbon atoms to which they are attached. The most preferred linkers are racemic 4-methoxymandelic acid, (+)-4-methoxymandelic acid, diphenylglycine and glycolic acid.

In a still further embodiment of the invention, a first linker is inserted between the presequence attached to the support and the $AA_1$–$AA_n$ sequence and a second linker is inserted between the presequence and the solid support with orthogonal cleavage conditions to the first linker enabling a selective cleavage of the second linker, e.g., by means of trifluoroacetic acid (TFA), trifluoromethanesulfonic acid (TFMSA), HBr, HCl, HF or a base such as ammonia, hydrazine, alkoxide or hydroxide to give the desired peptide $AA_1$–$AA_n$ linked to the presequence by means of said first linker, which is then optionally cleaved from the presequence.

Another important embodiment of the invention relates to agents for use in solid phase synthesis incorporating one or more of the above described features with relation to presequences and linkers.

A first aspect of this embodiment relates to an agent for use in solid phase peptide synthesis which contains a presequence and optionally one or more amino acids from the desired sequence has the general formula

wherein R is a solid support applicable in solid phase peptide synthesis, $Y_1$ is an amino acid sequence comprising from 3 to 9, preferably from 5 to 7 amino acid residues independently selected from native L-amino acids having a side chain functionality which is protected during the coupling steps and having a propensity factor Pα>0.57 and a propensity factor P≦1.10, e.g., Lys, Glu, Asp, Ser, His, Asn, Arg, Met or Gln, or the corresponding D-amino acid, AA' is an L- or D-amino acid residue, m is zero or an integer from 1 to 40 and X is hydrogen or an amino protective group.

A second aspect of this embodiment relates to an agent for use in solid phase peptide synthesis which contains a presequence, a preferably optically active cleavage linker and optionally one or more amino acids from the desired sequence and has the general formula

wherein X, AA', m, $Y_1$ and R are as defined above and $L_1$ is a preferably optically active linker which enables a selective cleavage of the bond to $AA'_m$. Preferred linkers are α-hydroxy or α-amino acids as described above.

A third aspect of this embodiment relates to an agent for use in solid phase peptide synthesis which contains a presequence, a first preferably optically active cleavage linker, a second linker enabling cleavage from the support and optionally one or more amino acids from the desired sequence and has the general formula

wherein X, AA', m, $Y_1$, R and $L_1$ are as defined above and $L_2$ is a linker which enables a selective cleavage from the solid support.

A fourth aspect of this embodiment relates to an agent for use in solid phase peptide synthesis which contains a linker enabling cleavage from the support, a presequence and optionally one or more amino acids from the desired sequence and has the general formula

wherein X, $AA'_1$, m, $Y_1$, R and $L_2$ is as defined above.

The specific conditions used in the experiments on which this invention is based are stated below under general procedures.

Generally speaking, apart from the novel and characteristic features related to the presequence and the novel cleavage linkers, the method according to the invention may be carried out under traditional conditions for solid phase peptide synthesis described in the literature referred to in the background art. Specifically, Fmoc groups may be deprotected by means of an amine such as piperidine or diazabicyclo[5,4,O]undec-7-ene (DBU). Side chain protective groups may be deprotected by means of an acid such as trifluoroacetic acid (TFA), trifluoromethanesulfonic acid (TFMSA) HBr, HCl or HF.

The solid support is preferably selected from functionalized resins such as polystyrene, polyacrylamide, polyethyleneglycol, cellulose, polyethylene, latex or dynabeads. If desired, C-terminal amino acids may be attached to the solid support by means of a common linker such as 2,4-dimethoxy-4'-hydroxy-benzophenone, 4-(4-hydroxy-methyl-3-methoxyphenoxy)-butyric acid (HMPB), 4-hydroxymethylbenzoic acid, 4-hydroxymethylphenoxyacetic acid (HMPA), 3-(4-hydroxymethylphenoxy)propionic acid or p-[(R,S)-α[1-(9H-fluoren-9-yl)methoxyformamido]-2,4-dimethoxybenzyl]-phenoxyacetic acid (AM).

The synthesis may be carried out batchwise or continuously on an automated or semi automated peptide synthesizer.

The individual coupling steps may be performed in the presence of a solvent, e.g., selected from acetonitrile, N,N-dimethylformamide (DMF), N-methylpyrrolidone (NMP), dichloromethane (DCM), trifluoroethanol (TFE), ethanol, methanol, water, mixtures of the mentioned solvents with or without additives such as perchlorate or ethylenecarbonate.

The individual couplings between two amino acids, an amino acid and the earlier formed peptide sequence or a peptide fragment and the earlier formed peptide sequence may be carried out according to usual condensation methods such as the azide method, mixed acid anhydride method, symmetrical anhydride method, carbodiimide method, active ester method such as pentafluorophenyl (Pfp), 3,4-dihydro-4-oxobenzotriazin-3-yl (Dhbt), benzotriazol-1-yl (Bt), 7-azabenzotriazol-1-yl (At), 4-nitrophenyl, N-hydroxysuccinic acid, imidoesters (NHS), acid chlorides, acid fluorides, in situ activation by O-(7-azabenzotriazol-1-yl)-1,1,3,3-tetramethyluronium hexafluorophosphate (HATU), O-(benzotriazol-1-yl)-1,1,3,3-tetramethyluronium hexafluorophosphate (HBTU), O-(benzotriazol-1-yl)-1,1,3,3-tetramethyluronium tetrafluoroborate (TBTU), or benzotriazolyl-oxy-tris-(dimethylamio)-phosphonium hexafluorophosphate (BOP).

The formed peptide may be cleaved from the support by means of an acid such as trifluoroacetic acid (TFA), trifluoromethanesulfonic acid (TFMSA), hydrogen bromide (HBr), hydrogen chloride (HCl), hydrogen fluoride (HF) or a base such as ammonia, hydrazine, an alkoxide or a hydroxide. Alternatively, the peptide is cleaved from the support by means of photolysis.

In the embodiment, where a linker is inserted between the presequence attached to the support and the $AA_1$–$AA_n$ sequence which enables a selective cleavage of said sequence, said cleavage may be made by means of an acid such as trifluoroacetic acid (TFA), trifluoromethanesulfonic acid (TFMSA), hydrogen bromide (HBr), hydrogen chloride (HCl), hydrogen fluoride (HF) or a base such as ammonia, hydrazine, an alkoxide or a hydroxide.

EXAMPLES

| Abbreviations | |
|---|---|
| AM, | p-[(R,S)-α[1-(9H-fluoren-9-yl)methoxyformamido]-2,4-dimethoxybenzyl]-phenoxyacetic acid |
| At, | 7-azabenzotriazol-1-yl |
| Boc, | tert. butyloxycarbonyl |
| BOP, | benzotriazolyl-oxy-tris-(dimethylamino)-phosphonium hexafluorophosphate |
| Bpoc, | biphenylpropyloxycarbonyl |
| Bt, | benzotriazol-1-yl |

| -continued | |
|---|---|
| Abbreviations | |
| tBu, | tert. butyl |
| DBU, | diazabicyclo[5,4,0]undec-7-ene |
| Ddz, | 3,5-dimethoxyphenylisopropyloxycarbonyl |
| DCC, | dicyclohexylcarbodiimide |
| DCM, | dichloromethane |
| DIC, | diisopropylcarbodiimide |
| DIEA, | N,N-diisopropylethylamine |
| DMAP, | 4-(N,N-dimethylamino)pyridine |
| Dhbt-OH, | 3,4-dihydro-3-hydroxy-4-oxo-1,2,3-benzotriazine |
| DMF, | N,N-dimethylformamide |
| Dts, | dithiasuccinyl |
| EDT, | ethanedithiol |
| FAB, | fast atom bombardment |
| Fmoc, | 9-fluorenylmethyloxycarbonyl |
| HATU, | O-(7-azabenzotriazol-1-yl)-1,1,3,3-tetramethyluronium hexaflurophosphate |
| HBTU, | O-(benzotriazol-1-yl)-1,1,3,3-tetramethyluronium hexafluorophosphate |
| HMPA, | 4-hydroxymethylphenoxyacetic acid |
| HMPB, | 4-(4-hydroxymethyl-3-methoxyphenoxy)-butyric acid |
| HObt, | 1-hydroxybenzotriazole |
| HOAt, | 1-hydroxy-7-azobenzotriazole |
| HPLC, | high pressure liquid chromatography |
| MCPS, | multiple column peptide synthesis |
| MHC, | major histocompatibility complex |
| MMa, | 4-methoxymandelic acid |
| NMR, | nuclear magnetic resonance |
| NHS, | N-hydroxy-succinic acid imido ester |
| NMP, | N-methylpyrrolidone |
| NPS, | nitrophenylsulfenyl |
| Mtr, | 4-methoxy-2,3,6-trimettiylpheriylsulfonyl |
| PAM, | phenylacetamidomethyl |
| Pbf, | 2,2,4,6,7-pentamehtyldihydrobeiizofuran-5-sulfonyl |
| PEG-PS, | polyethyleneglycol grafted on polystyrene |
| PepSyn Gel, | polydimethylacrylamide resin functionalized with sarcosine methylester |
| PepSyn K, | Kieselguhr supported polydimethylacrylamide resin functionalized with sarcosine methylester |
| Pfp, | pentafluorophenyl |
| Pmc, | 2,2,5,7,8-pentamethylchorman-6-sulfonyl |
| Poc, | phenylisopropyloxycarbonyl |
| TBTU, | O-(benzotriazol-1-yl)-1,1,3,3 tetramethyluronium tetrafluoroborate |
| TFA, | trifluoroacetic acid |
| TFE, | trifluorethanol |
| TFMSA, | trifluoromethanesulfonic acid |
| Tmz, | 2,4,5-tetramethylbenzyloxycarboxyl |

General Procedures: Peptide Synthesis

Apparatus and Synthetic Strategy

Peptides were synthesized either batchwise in a polyethylene vessel equipped with a polypropylene filter for filtration or in the continuous-flow version of the polyamide solid-phase method (Dryland, A. and Sheppard, R. C. (1986) J. Chem. Soc. Perkin Trans. I, 125–137) on a fully automated peptide synthesizer (Cameron, L., Meldal, M. and Sheppard, R. C (1987), J. Chem. Soc. Chem. Commun. 270–272) using 9-fluorenylmethyloxycarbonyl (Fmoc) or tert. Butyloxycarbonyl, (Boc) as N-α-amino protecting group and suitable common protection groups for side-chain functionalities.

Solvents

Solvent DMF (N,N-dimethylformamide, Riedel de-Häen, Germany) was purified by passing it through a column packed with a strong cation exchange resin (Lewatit S 100 MB/H strong acid, Bayer AG Leverkusen, Germany) and analyzed for free amines prior to use by addition of 3,4-dihydro-3-hydroxy-4-oxo-1,2,3-benzotriazine (Dhbt-OH) giving rise to a yellow color (Dhbt-O⁻ anion) if free amines are present. Solvent DCM, (dichloromethane, analytical grade, Riedel de-Häen, Germany) was used directly without purification.

Amino Acids

Fmoc-protected amino acids and corresponding pentaflorophenyl (Pfp) esters were purchased from MilliGen, UK, NovaBiochem, Switzerland and Bachem, Switzerland, and the Dhbt-esters from NovaBiochem, Switzerland in suitable side-chain protected forms. Bocprotected amino acids were purchased from Bachem, Switzerland.

Coupling Reagents

Coupling reagent diisopropylcarbodiimide (DIC) was purchased from Riedel de-Häen, Germany and distilled prior to use, dicyclohexylcarbodiimide (DCC) was purchased from Merck-Schuchardt, München, Germany, and purified by distillation. O-Benzotriazolyl-N,N,N',N'-tetramethyluronium tetrafluoroborate (TBTU) was purchased from PerSeptive Biosystems GmbH Hamburg, Germany.

Linkers

Linkers HMPA, Novabiochem, Switzerland; 4-hydroxymethylbenzoic acid, Novabiochem; 4-methoxymandelic acid, Aldrich, Germany; HMPB, Novabiochem; AM, Novabiochem; 3-(4-hydroxymethylphenoxy)propionic acid, Novabiochem, was coupled to the resin as a preformed 1-hydroxybenzotriazole (HObt) ester generated by means of DIC. Racemic 4-methoxymandelic acid (98% pure, Aldrich, Germany) was used directly as linker, or as described below, resolved by treatment with (+)-cinchonine (85% pure, Aldrich, Germany).

Resolution of (+/−)-4-methoxymandelic acid (McKenzie, A., Pirie, D. J. C. (1936), Berichte 69, 868, & Knorr, E. (1904), Berichte 37, 3172)

(+/−)-4-Methoxymandelic acid (10 g, 54.89 mmol; Aldrich, 98%) was dissolved in 500 ml hot water (60–80° C.) and the solution was decanted while still warm in order to remove insoluble impurities. (+)-Cinchonine (16.16 g, 54.89 mmol, Aldrich, 85%, $[a]D^{20}$=+211° (litt.: +228°) was added to the hot solution in small portions. The solution became clear after 15 min stirring at 60–80° C. and was cooled in ice. After 1 h, the precipitate was collected by filtration and dried in a dessicator overnight, yielding 9.9 g of the chinconine salt. The salt was recrystallized from boiling water (80 ml), the solution decanted while still warm and then cooled in ice. The precipitate was collected by filtration after 1 h, washed three times with cold water, and dried in a dessicator overnight yielding 7.84 g 16.45 mmol). The chinconine salt (2 g, 4.2 mmol) was dissolved in 40 ml 2N HCl and immediately extracted with 3×30 ml diethylether. The ether phase was dried over $Na_2SO_4$ and evaporated to dryness yielding 0.55 g 4-methoxymandelic acid. The optical purity of the liberated 4-methoxymandelic acid was estimated to 18.5% ($[a]D^{20}$=+27°). After a second recrystallization of the chinconine salt followed by liberation of the mandelic acid as described above, the optical purity was estimated to 69.0% ($[a]D^{20}$=+100.8°). A third recrystallization resulted in an optical purity of 95.8% ($[a]D^{20}$=+140.0°).

Solid Supports

Peptides synthesized according to the Fmoc-strategy were synthesized on three different types of solid support using 0.05 M or higher concentrations of Fmoc-protected activated amino acid in DMF: 1) PEG-PS (polyethyleneglycol grafted on polystyrene; TentaGel S $NH_2$ resin, 0.27 mmol/g, Rapp Polyinere, Germany or NovaSyn TG resin, 0.29 mmol/g, Novabiochem, Switzerland); 2) PepSyn Gel (polydimethylacrylamide resin functionalized with sarcosine methylester, 1.0 mmol/g; MilliGen, UK). 3) PepSyn K (Kieselguhr supported polydimethylacrylamide resin functionalized with sarcosine methylester 0.11 mmol/g; MilliGen, UK).

Peptides synthesized according to the Boc-strategy were synthesized on a Merrifield-resin (polystyrenedivinylbenzene) with the first amino acid attached (Novabiochem, Switzerland).

Catalysts and Other Reagents

Diisopropylethylamine (DIEA) was purchased from Aldrich, Germany, and ethylenediamine from Fluka, Switzerland, piperidine from Riedel-de Häen, Frankfurt, Germany. 4-(N,N-dimethylamino)pyridine (DMAP) was purchased from Fluka, Switzerland and used as a catalyst in coupling reactions involving symmetrical anhydrides. 3,4-dihydro-3-hydroxy-4-oxo-1,2,3-benzotriazine (Dhbt-OH) was obtained from Fluka, Switzerland, and 1-hydroxybenzotriazole (HObt) from NovaBiochem, Switzerland.

Coupling-Procedures

The first amino acid was coupled as a symmetrical anhydride in DMF generated from the appropriate N-α-protected amino acid and DIC. The following amino acids were coupled as Pfp- or Dhbt-esters or as preformed HObt esters made from appropriate N-α-protected amino acids and HObt by means of DIC or TBTU in DMF. In the case of Fmoc, all acylations were checked by the ninhydrin test performed at 80° C. in order to prevent Fmoc deprotection during the test (Larsen, B. D., and Holm, A. (1994), Int. J. Peptide & Protein Res. 43,1–9).

Deprotection of the N-α-Amino Protecting Group

Deprotection of the Fmoc group was performed by treatment with 20% piperidine in DMF (1×3 and 1×7 min when synthesized batchwise) or by flowing the deprotection solvent through the resin (10 min, flow rate 1 ml/min using continuous flow synthesis), followed by wash with DMF until no yellow color (Dhbt-O-) could be detected after addition of Dhbt-OH to the drained DMF.

Deprotection of the Boc group was performed by treatment with 50% TFA in DCM (v/v) 1×1.5 min and 1×20 min followed by wash 6×9 min each with DCM, neutralization with 10% triethylamine in DCM (v/v) 2×1.5 min each, followed by 6×9 min wash with DCM.

Cleavage of Peptide from Resin with Acid

Peptides were cleaved from the resins by treatment with 95% triflouroacetic acid (TFA, Halocarbon Products Corporation, U.S.A.; Biesterfeld & Co. Hamburg, Germany)-water v/v at r.t. for 2 h. The filtered resins were washed with 95% TFA-water and filtrates and washings were evaporated under reduced pressure. The residue was washed with ether and freeze dried from acetic acid-water. The crude freeze dried product was analyzed by high-performance liquid chromatography (HPLC) and identified by matrix assisted laser desorption ionization time of flight mass spectrometry (MALDI TOF MS) or by electrospray ionization mass spectrometry (ESMS).

Cleavage of Peptide from Resin with Base

The dried resin (1 g) was treated with 1M sodium hydroxide (10 ml) at 4° C. and left for 15 min at r.t. The resin was filtered into a flask containing 10% aq. acetic acid. The peptide was isolated by lyophilization and submitted to gel filtration.

Cleavage of Peptide from Resin with TFMSA

The dried resin (250 mg) was placed in a round-bottomed flask with a stirring bar. Thioanisole/ethanedithiol 2:1, 750 µl) was added, the mixture chilled in ice, 5 ml TFA was added and the mixture was stirred for 5–10 min. TFMSA (500 μl) was added dropwise and the reaction continued at r.t. for 30–60 min. The peptide was precipitated after addition of ether.

Deprotection of Side Chain Protective Groups

The side chains were generally deprotected simultaneously with the cleavage of the peptide from the resin.

Preformed HObt-Ester

Method a. 3 eq. N-α-amino protected amino acid was dissolved in DMF together with 3 eq. HObt and 3 eq. DIC. The solution was left at r.t. for 10 minutes and then added to the resin, which had been washed with a solution of 0.2% Dhbt-OH in DMF prior to the addition of the preactivated amino acid.

Method b. 3 eq. N-α-amino protected amino acid was dissolved in DMF together with 3 eq. HObt, 3 eq. TBTU and 4.5 eq. DIEA. The solution was left at r.t. for 5 minutes and then added to the resin.

Preformed Symmetrical Anhydride 6 eq. N-α-amino protected amino acid was dissolved in DCM and cooled to 0° C. DCC (3 eq.) was added and the reaction continued for 10 min. The solvent was removed in vacuo and the remains dissolved in DMF. The solution was filtered and immediately added to the resin followed by 0.1 eq. of DMAP.

Estimation of the Coupling Yield of the First N-α-Amino Protected Amino Acid

3–5 mg dry Fmoc-protected peptide-resin was treated with 5 ml 20% piperidine in DMF for 10 min at r.t. and the UV absorption for the dibenzofulvenepiperidine adduct was estimated at 301 nm. The yield was determined using a calculated extension coefficient $e_{301}$ based on a Fmoc-Ala-OH standard.

In case of Boc-protection, the coupling was estimated according to the ninhydrin-method after removal of the Boc-group (Sarin, V. Y., Kent, S. B. H., Tam, J. P. and Merrifield, R. B. (1981), Anal. Biochem. 117, 147–157).

Peptide Synthesis on PepSyn K Resin

Dry PepSyn K (ca 500 mg), was covered by ethylenediamine and left at r.t. overnight. The resin was drained and washed with DMF 10×15 ml, 5 min each. After draining, the resin was washed with 10% DIEA in DMF v/v (2×15 ml, 5 min each) and finally washed with DMF until no yellow color could be detected by addition of Dhbt-OH to the drained DMF. 3 eq. HMPA, 3 eq. HObt and 3 eq. DIC were dissolved in 10 ml DMF and left for activation for 10 min, after which the mixture was added to the resin and the coupling continued for 24 h. The resin was drained and washed with DMF (10×15 ml, 5 min each), and the acylation was checked by the ninhydrin test. The first amino acid was coupled as the side chain protected preformed symmetrical anhydride (see above), and the coupling yields estimated as described above. It was in all cases better than 70%. The synthesis was then continued either as "continuous-flow" or as "batchwise" as described below.

Continued Peptide Synthesis on PepSyn K Using Continuous-Flow Technique

The resin (ca. 500 mg) with the first amino acid attached was placed in a column connected to the fully automated peptide synthesizer. The Fmoc group was deprotected as described above. The remaining amino acids according to the sequence were coupled as Fmoc protected, if necessary, side chain protected, Pfp esters (3 eq.) with the addition of Dhbt-OH (1 eq.). The end-point of each coupling was determined automatically by monitoring the disappearance of the yellow color of the Dhbt-OH anion spectrophotometrically. After completed synthesis, the peptide resin was washed with DMF (10 min flow rate 1 ml/min), DCM (3×5 ml, 3 min each) and finally diethyl ether (3×5 ml each), removed from the column and dried in vacuo.

Continued Batchwise Peptide Synthesis on PePSyn

The resin (ca. 500 mg) with the first amino acid attached was placed in a polyethylene vessel equipped with a polypropylene filter for filtration, and the Fmoc-group deprotected as described above. The remaining amino acids according to the sequence were coupled as preformed Fmoc-protected, if necessary, side chain protected, HObt esters (3 eq.) in DMF (5 ml) prepared as described above. The couplings were continued for 2 h unless otherwise specified. Excess reagent was then removed by DMF washing (12 min, flow rate 1 ml/min) All acylations were checked by ninhydrin test performed at 80° C. After completed synthesis, the peptide-resin was washed with DMF (10 min, flow rate 1 ml/min), DCM and finally diethyl ether (5×5 ml, 1 min each) and finally diethyl ether (5×5 ml, 1 min each) and dried in vacuo.

Batchwise Peptide Synthesis on PEG-PS

TentaGel S $NH_2$ or NovaSyn TG resin (250 mg, 0.27–0.29 mmol/g) was placed in a polyethylene vessel equipped with a polypropylene filter for filtration. The resin was swelled in DMF (5 ml), and treated with 20% piperidine in DMF to secure the presence of nonprotonated amino groups on the resin. The resin was drained and washed with DMF until no yellow color could be detected after addition of Dhbt-OH to the drained DMF. HMPA (3 eq.) was coupled as a preformed Hobt-ester as described above and the coupling was continued for 24 h. The resin was drained and washed with DMF (5×5 ml, 5 min each) and the acylation checked by the ninhydrin test. The first amino acid was coupled as a preformed symmetrical anhydride as described above. The coupling yields of the first Fmoc-protected amino acids were estimated as described above. It was in all cases better than 60%. The following amino acids according to the sequence were coupled as preformed Fmoc-protected, if necessary side chain protected, HObt esters (3 eq.) as described above. The couplings were continued for 2 h, unless otherwise specified. The resin was drained and washed with DMF (5×5 ml, 5 min each) in order to remove excess reagent. All acylations were checked by the ninhydrin test performed at 80° C. After completed synthesis, the peptide-resin was washed with DMF (3×5 ml, 5 min each), DCM (3×5 ml, 1 min each) and finally diethyl ether (3×5 ml, 1 min each) and dried in vacuo.

Batchwise Peptide Synthesis on Pep-Syn Gel

Dry PepSyn Gel resin (500 mg, 1 mmol/g) was placed in a polyethylene vessel equipped with a polypropylene filter for filtration. The resin was swelled in ethylenediamine (15 ml) and gently agitated by shaking for 20 h. The resin was drained and washed with DMF (10×15 ml, 5 min each). After draining, the resin was washed with 10% DIEA in DMF v/v (2×15 ml, 5 min each) and finally washed with DMF (5×15 ml, 5 min each) until no yellow color could be detected after addition of Dhbt-OH to the drained DMF. HMPA (3 eq.) was coupled as a preactivated HObt-ester as described above (method a) and the coupling was continued for 24 h. The resin was drained and washed with DMF (5×15 ml, 5 min each). The acylation was checked by the ninhydrin test. The first amino acid was coupled as preformed side chain protected symmetrical anhydride as described above.

The coupling yields of the first Fmoc-protected amino acids were estimated as described above. It was in all cases better than 70%. The remaining amino acids according to the sequence were coupled as preformed Fmoc-protected, if necessary side chain protected, Hobt esters (3 eq.) as described above (method a). The couplings were continued for 2 h and, if necessary, double coupled overnight. The resin was drained and washed with DMF (5×5 ml, 5 min each) in order to remove excess reagent. All acylations were checked by the ninhydrin test performed at 80° C. The Fmoc group was deprotected as described above. After completed synthesis, the peptide-resin was washed with DMF (3×15 ml, 5 min each), DCM (3×15 ml, 2 min each) and finally diethyl ether (3×15 ml, 2 min each) and dried in vacuo.

HPLC Conditions

HPLC was performed on a Waters 600 E instrument equipped with a Waters 996 Photodiode array detector with a Waters Radial Pak 8×100 mM $C_{18}$ reversed-phase column. Buffer A was 0.1 vol % TFA in water and buffer B was 90 vol % acetonitrile, 9.9 vol % water and 0.1 vol % TFA. The buffers were pumped through the column at a flow rate of 1.5 ml/min using the gradient: 1. Linear gradient from 0%–70% B (20 min), linear gradient from 70–100% B (1 min) isocratic 100% B (5 min). 2. Isocratic with 0% B (2 min), linear gradient from 0–50% B (23 min), linear gradient from 50–100% B (5 min), isocratic 100% B (5 min).

Mass Spectroscopy

Matrix assisted laser desorbtion ionization time-of-flight (MALDI TOF) mass spectra were obtained on a Fisons TofSpec E instrument. Electrospray ionization mass spectra were obtained on a Finnigan Mat LCQ instrument equipped with an electrospray (ESI) probe (ES-MS).

Syntheses of H-$(Ala)_n$-$(Lys)_m$-OH Oligomers

To investigate the problems described above with reference to B. D. Larsen, C. Larsen, and A. Holm., Peptides 1990; E. Giralt and D. Andreu, (Eds)., 1991 ESCOM Science Publishers B.V., p. 183–185 & Larsen, B. D., and Holm, A. (1994), Int. J. Peptide & Protein Res. 43,1–9, further, the degree to which the β-sheet formation of the homo oligo-alanine chain may be affected by inclusion of a shorter peptide sequence, a presequence, in the chain at the C-terminus was addressed. This question is associated with the fact that protein structures and polypeptide sequences may have stretches of well defined structures dependent on the amino acids in the sequence and of preceding amino acids. As mentioned earlier, Chou and Fasman's investigations (Chou, P. Y. and Fasman, G. D. (1978), Ann. Rev. Biochem. 47, 251–276.) on protein structures have led to recognition of classes of amino acids which are defined as predominantly α-helix inducing β-sheet or random coil inducing. Although it a priori may be assumed that similar predictions may apply for homo oligo alanines or leucines it was pointed out, however, in Larsen, B. D., and Holm, A. (1994), Int. J. Peptide & Protein Res. 43, 1–9. that Chou and Fasman rules do not predict homo oligoalanine or leucine peptides as β-sheet forming chains. Furthermore, Chou and Fasman's rules cannot be expected to apply during peptide synthesis on a resin and do clearly not apply when side-chain protected amino acids are part of the synthesis.

Peptide Synthesis of Individual Peptides

Synthesis of H-$Ala_{10}$-Lys-OH (SEQ ID NO:3) (Comparison)

500 mg Fmoc-Lys(Boc) PepSyn KA resin (0.086 mmol/g) was used for synthesis according to "continuous-flow technique".

Figure 2:
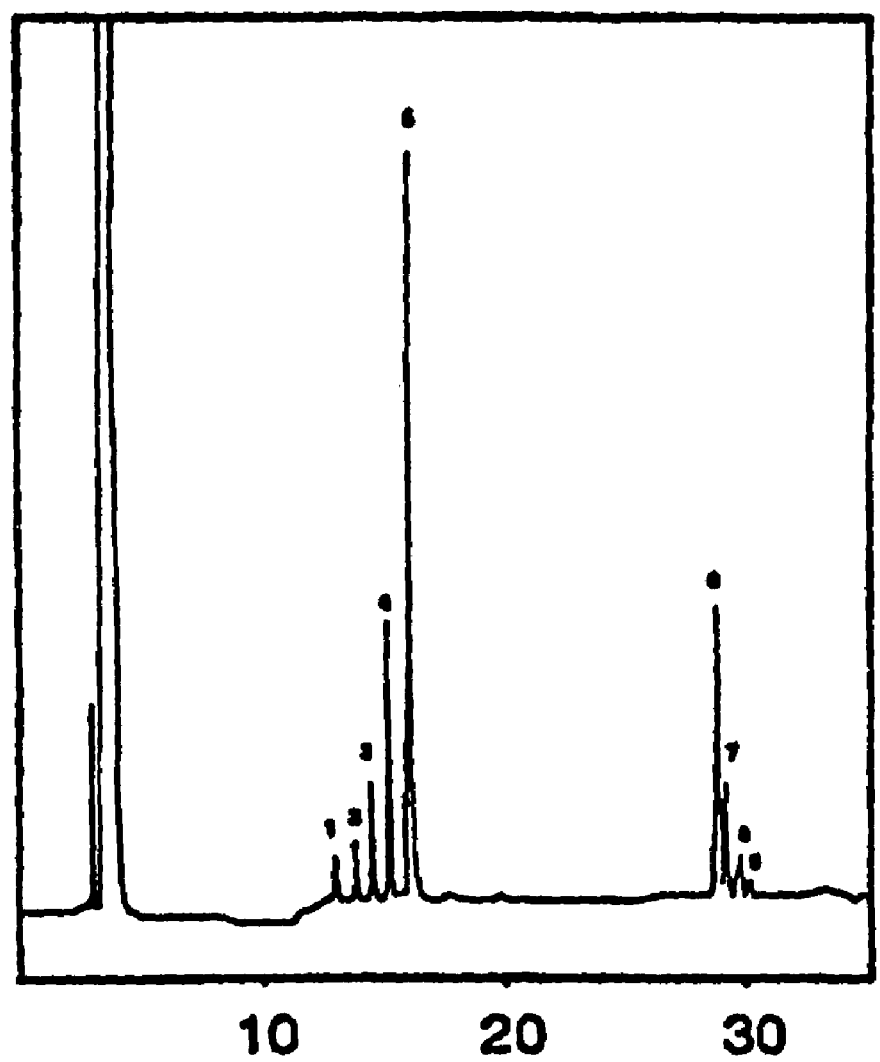
FIG. 2 is an HPLC of crude H-Ala$_{10}$-Lys-OH (SEQ ID NO:3) showing a substantial amount of deletion peptides (peak 1, 2, 3 and 4) and incompletely Fmoc-deprotected peptides (peak 6, 7, 8 and 9) besides the target peptide (peak 5).
Figure 3:
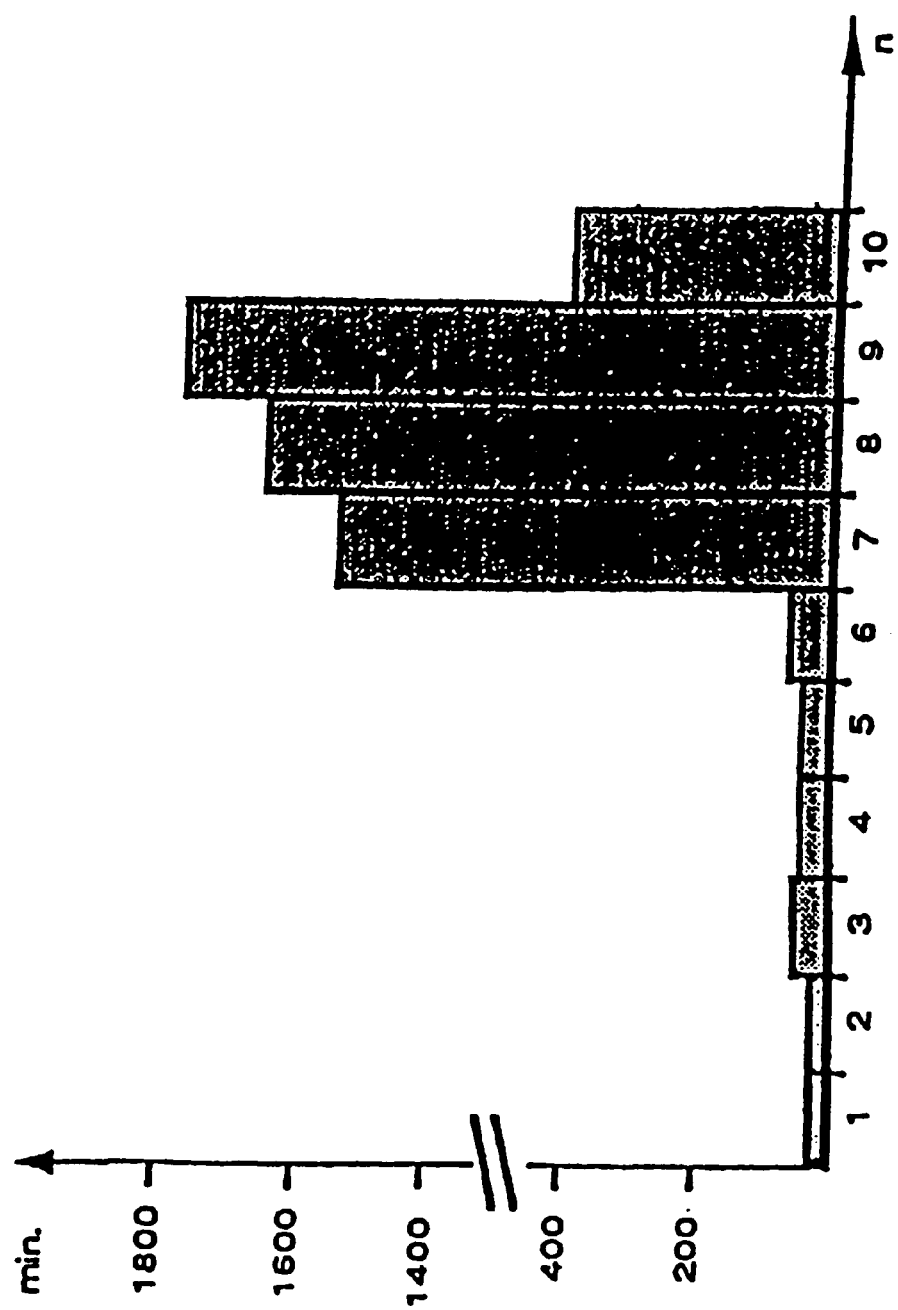
FIG. 3 is a diagram showing sequential coupling times for each of the alanines in the synthesis of H-Ala$_{10}$-Lys-OH (SEQ ID NO:3).

The crude freeze dried product was analyzed by HPLC and found to be a complicated mixture comprising the target peptide (n=10) as well as deletion peptides corresponding to n=6, 7, 8, and 9 and deletion peptides with the Fmoc group still attached to the N-terminal where n=6, 7, 8, and 9 respectively (see FIG. 2). The identity of the individual peptides was confirmed by MALDI TOF MS.

Synthesis of H-$Ala_{10}$-$Lys_3$-OH (SEQ ID NO:4)

500 mg Fmoc-Lys(Boc) PepSyn KA resin (0.086 mmol/g) was used for synthesis according to "continuous-flow technique".

The crude freeze-dried product was analyzed by HPLC and found to be homogeneous without deletion and Fmoc-protected sequences. Yield 91.0%. The purity was found to be better than 98% according to HPLC (see FIG. 4). The identity of the peptide was confirmed by MALDI TOF MS.

Synthesis of H-$Ala_{10}$-OH (SEQ ID NO:6)

500 mg Fmoc-Lys(Boc) PepSyn KA resin (0.086 mmol/g) was used for synthesis according to the "continuous-flow technique".

Figure 6:
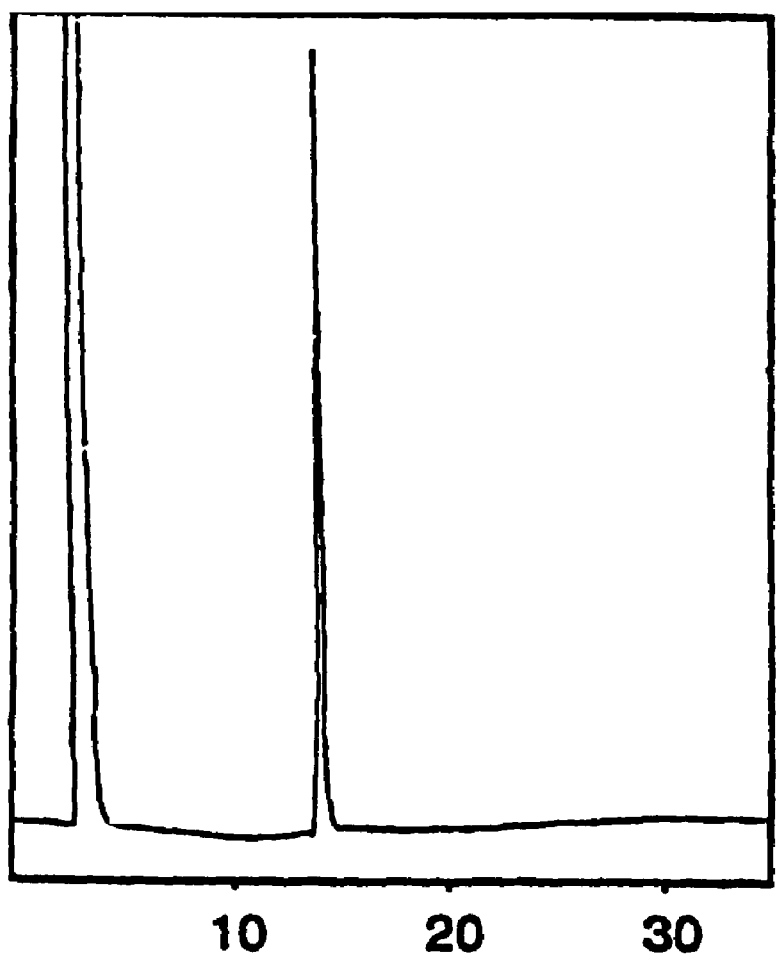
FIG. 6 is an HPLC of H-Ala$_{10}$-Lys$_6$-OH (SEQ ID NO:6). No deletion peptides were observed.

The crude freeze dried product was analyzed by HPLC and found to be homogeneous without deletion and Fmoc-protected sequences. Yield 90.9%. The purity was found to be better than 98% according to HPLC (see FIG. 6). The identity of the peptide was confirmed by ES MS.

Synthesis of H-$Ala_{20}$-$Lys_3$-OH (SEQ ID NO:5)

500 mg Fmoc-$Ala_{10}$-$(Lys(Boc))_3$ PepSyn KA resin (SEQ ID NO:28) (from the synthesis of H-$Ala_{10}$-$Lys_3$-OH) (SEQ ID NO:4) was used for synthesis according to the "continuous-flow technique" and the synthesis was continued.

Figure 5:
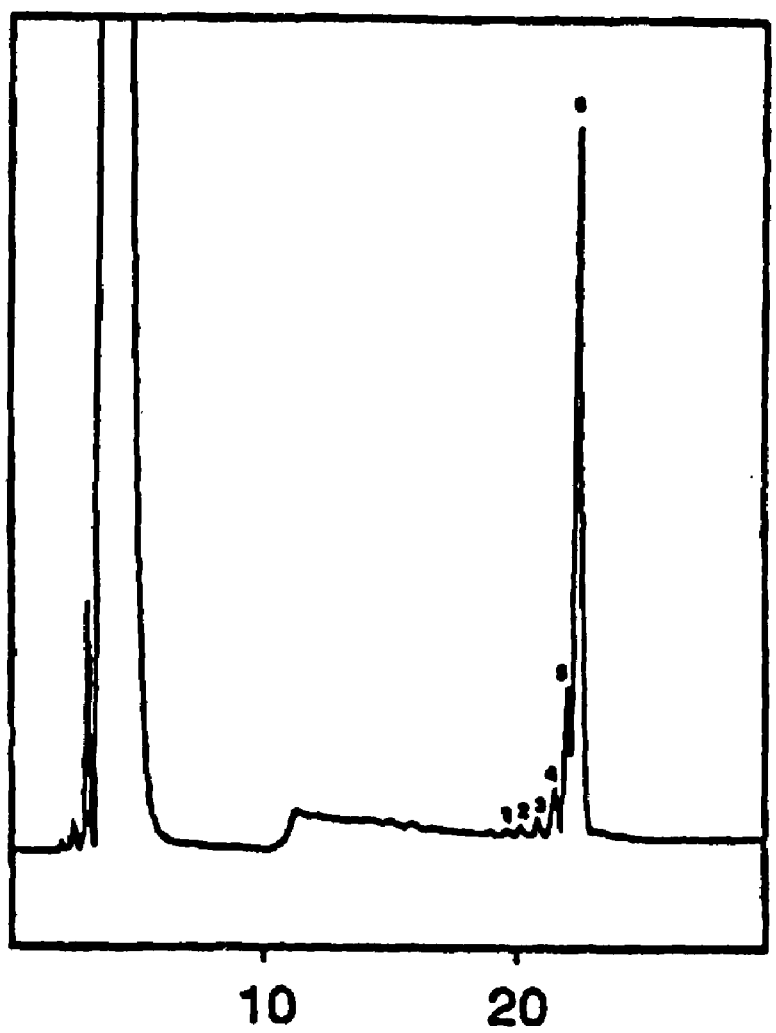
FIG. 5 is an HPLC of H-Ala$_{20}$-Lys$_3$-OH (SEQ ID NO:5) showing deletion peptides (peak 1, 2, 3, 4 and 5) besides the target peptide (peak 6).

The crude freeze dried product was analyzed by HPLC and found to comprise the target peptide H-$Ala_n$-$Lys_3$-OH (SEQ ID NO:30)(n=20) as well as deletion peptides corresponding to n=19, 18, 17 and 16 (see FIG. 5). Fmoc-protected sequences were not detected. The identity of the peptides were confirmed by ES MS.

Synthesis of H-$Ala_{20}$-$Lys_6$-OH (SEQ ID NO:7)

500 mg Fmoc-Lys(Boc) PepSyn KA resin (0.086 mmol/g) was used for synthesis according to the "continuous-flow technique".

The crude freeze dried product was analyzed by HPLC and found to be homogeneous without deletion and Fmoc-protected sequences. Yield 91.4%. The purity was found to be better than 98% according to HPLC (see FIG. 7). The identity of the peptide was confirmed by ES MS.

Synthesis of H-$Ala_{20}$-Lys-$(Gly-Lys)_3$-OH SEQ ID NO:29)

500 mg Fmoc-Lys(Boc) PepSyn KA resin (0.086 mmol/g) was used for synthesis according to the "continuous-flow technique".

The crude freeze-dried product was analyzed by HPLC. It was found to be better than 98% pure without deletion and Fmoc-protected sequences. Yield 97%. The identity of the peptide was confirmed by ES MS.

Synthesis of H-$Ala_{10}$-Lys-OH (SEQ ID NO:3) Using (Lys(Boc))$_6$ (SEQ ID NO:22) as Presequence and HMPA as Linker (H-$Ala_{10}$-Lys(Boc)-$OCH_2$-$PhOCH_2CO$-(Lys(Boc)))$_6$-$NHCH_2$-$CH_2NH$ PepSyn K)(SEQ ID NO:31)

500 mg dry PepSyn K (0.1 mmol/g) was covered by ethylenediamine (5 ml) and left at r.t. overnight. The resin was drained and washed with DMF 10×15 ml, 5 min each. After draining the resin was washed with 10% DIEA in DMF v/v (2×15 ml, 5 min each) and finally washed with DMF until no yellow color could be detected by addition of Dhbt-OH to the drained DMF. The derivatized resin was used for synthesis according to the "continuous-flow technique".

The first 6 lysines forming the presequence were coupled as Fmoc-Lys(Boc)-Pfp esters (3 eq.) with the addition of Dhbt-OH (1 eq.). The end-point of each coupling was determined automatically as described above. The Fmoc group was cleaved as described above. After finishing the presequence, 3 eq. HMPA coupled as a preactivated HObt ester as described above was introduced at the top of the column. The synthesizer was operated in recirculation mode for 2 h and excess of reagent was then removed by DMF washing (12 min, flow rate 1 ml/min). A small resin-sample was removed in order to check the acylation by the ninhydrin test. The next amino acid according to the sequence was coupled as preformed side chain protected symmetrical anhydride as described above and introduced at the top of the column together with (0.1 eq.) DMAP and the synthesizer was operated in recirculation mode for 90 min. Excess reagent was then removed by DMF washing (12 min, flow rate 1 ml/min). A small resin-sample was removed in order to check the coupling yield, which was estimated as earlier described and found to be 84%. The synthesis was then continued by cleavage of the Fmoc group as described above. The remaining amino acids according to the sequence were coupled as Fmoc-protected, if necessary side chain protected, Pfp esters (3 eq.) with addition of Dhbt-OH (1 eq.). The end-point of each coupling was determined automatically as described above. After completed synthesis, the peptide-resin was washed with DMF (10 min, flow rate 1 ml/min), DCM (3×5 ml, 1 min each) and finally diethyl ether (3×5 ml, 1 min each), removed from the column and dried in vacuo.

The peptide was cleaved from the resin as described above.

Figure 8:
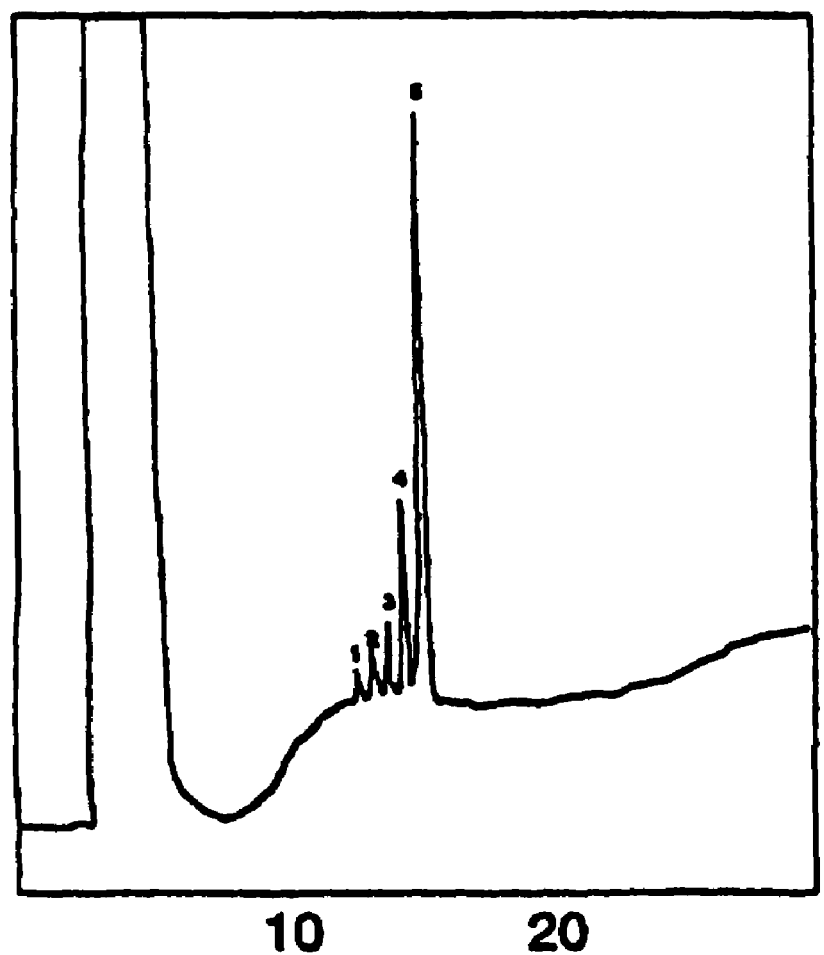
FIG. 8 is an HPLC of H-Ala$_{10}$-Lys-OH (SEQ ID NO:3) prepared by introduction of an HMPA linker. Deletion peptides were observed (from Ala$_{10}$-Lys(tBoc)-HMPA-(Lys (tBoc))$_6$-resin) (SEQ ID NO:10).

The crude freeze dried product was analyzed by HPLC and found to comprise the target peptide H-Ala$_n$-Lys-OH (SEQ ID NO:34)(n=10) as well as deletion peptides corresponding to n=9, 8, 7 and 6 (see FIG. 8). Fmoc-protected sequences were not detected. The identity of the peptides were confirmed by MALDI TOF MS.

Synthesis of H-Ala$_{10}$-Lys-OH(SEQ ID NO:3) Using (+/−) 4-methoxymandelic Acid as Linker (H-Ala$_{10}$-Lys(Boc)-OCH-(4-MeOPh)CONHCH$_2$CH$_2$NH PepSyn K Resin) (SEQ ID NO:32)

500 mg dry PepSyn K (0.1 mmol/g) was treated with ethylenediamine as described above. The derivatized resin was used for synthesis according to the "continuous-flow technique". 10 eq. (+/−)-4-methoxymandelic acid, 10 eq. HObt and 10 eq. DIC dissolved in 5 ml DMF, preactivated for 10 min were introduced at the top of the column and the synthesizer was operated in recirculation mode for 2 h. Excess of reagent was then removed by DMF washing (12 min, flow rate 1 ml/min). A small resin-sample was removed in order to check the acylation by the ninhydrin test. The first amino acid according to the sequence was coupled as Fmoc protected and side chain protected preformed symmetrical anhydride as described above and introduced at the top of the column together with (0.1 eq.) DMAP and the synthesizer was operated in recirculation mode for 90 min. Excess reagent was then removed by DMF washing (12 min, flow rate 1 ml/min). A small resin-sample was removed in order to check the coupling yield, which was estimated as described above and found to be 75%. The synthesis was then continued by cleavage of the Fmoc group as earlier described. The remaining amino acids according to the sequence were coupled as Fmoc-protected Pfp esters (3 eq.) with the addition of Dhbt-OH (1 eq.). The end-point of each coupling was determined automatically as described above. After completed synthesis, the peptide-resin was washed with DMF (10 min, flow rate 1 ml/min), DCM (3×5 ml, 1 min each) and finally diethyl ether, removed from the column and dried in vacuo.

Figure 9:
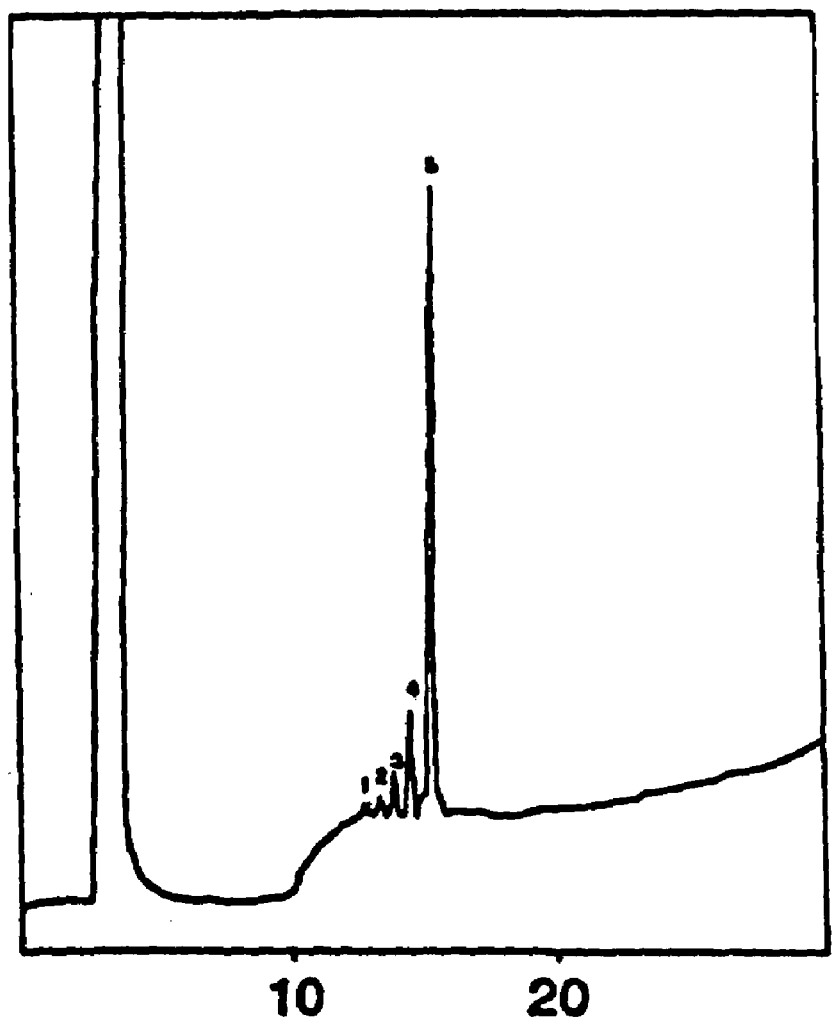
FIG. 9 is a similar HPLC of H-Ala$_{10}$-Lys-OH (SEQ ID NO:3) prepared by using an MMa-linker showing a significant reduction the amount of deletion peptides compared to FIG. 8 (from Ala$_{10}$-Lys-MMa-Lys(tBoc))$_6$-resin) (SEQ ID NO:11).

The peptide was cleaved from the resin as earlier described and lyophilized from acetic acid-water. The crude freeze dried product was analyzed by HPLC and found to comprise the target peptide H-Alan-Lys-OH (n=10) as well as deletion peptides corresponding to n=9, 8, 7 and 6 (FIG. 9). The identity of the peptides were confirmed by MALDI TOF MS.

Synthesis of H-Ala$_{10}$-Lys-OH (SEQ ID NO:3) Using (Lys (Boc))$_6$ (SEQ ID NO:22) as Presequence and (+/−)-4-methoxymandelic Acid as Linker (H-Ala$_{10}$-Lys(Boc)-OCH-(4MeOPh)CO-(Lys(Boc))$_6$-NHCH$_2$CH$_2$NH PepSyn K Resin) (SEQ ID NO:33)

500 mg dry PepSyn K (0.1 mmol/g) was treated with ethylenediamine as described above. The derivatized resin was used for synthesis according to the "continuous-flow technique". The first 6 Lysines forming the presequence were coupled as Fmoc-protected and side chain protected Pfp esters (3 eq.) with the addition of Dhbt-OH (1 eq.). The end-point of each coupling was determined automatically as described above. The Fmoc group was cleaved as described above. After completed synthesis, of the presequence, 10 eq. (+/−)-4-methoxymandelic acid was coupled as preactivated HObt-ester as earlier described and introduced at the top of the column. The synthesizer was operated in recirculation mode for 2 h and excess reagent was then removed by DMF washing (12 min, flow rate 1 ml/min). A small resin-sample was removed in order to check the acylation by the ninhydrin test. The next amino acid according to the sequence was coupled as Fmoc protected and side chain protected preformed symmetrical anhydride as earlier described and introduced at the top of the column together with (0.1 eq.) DMAP. The synthesizer was operated in recirculation mode for 90 min and excess reagent was then removed by DMF washing (12 min, flow rate 1 ml/min). A small resin-sample was removed in order to check the coupling yield, which was estimated as described above and found to be 68%. The synthesis was then continued by cleavage of the Fmoc group as earlier described. The remaining amino acids according to the sequence were coupled as Fmoc protected Pfp esters (3 eq.) with the addition of Dhbt-OH (1 eq.). The end-point of each coupling was determined automatically as described above. After completed synthesis, the peptide-resin was washed with DMF (10 min, flow rate 1 ml/min), DCM (3×5 ml min, flow rate 1 ml/min) and finally diethyl ether (3×5 ml min, flow rate 1 ml/min), removed from the column and dried in vacuo. The peptide was cleaved from the resin as earlier described and freeze dried from acetic acid-water. The crude freeze dried product was analyzed by HPLC and found to comprise the target peptide H-Ala$_n$-Lys-OH (SEQ ID NO:34)(n=10) as well as deletion peptides corresponding to n=9, 8, 7 and 6. The amount of deletion peptides was found to be significantly reduced compared to the synthesis of SEQ ID NOS: 31 and 33 as described above (see FIG. 9). Fmoc-protected sequences were not detected. The identity of the peptides were confirmed by MALDI TOF MS.

Synthesis of H-Ala$_{10}$-Lys-OH (SEQ ID NO:3) Using (Lys (Boc))$_6$ (SEQ ID NO:22) as Presequence and (+)-4-methoxymandelic Acid as Linker (H-Ala$_{10}$-Lys(Boc)-OCH-4-MeOPh)Co(Lys(Boc))$_6$-NHCH$_2$CH$_2$NH. PepSyn K Resin) (SEQ ID NO:33)

Dry PepSyn K (ca 500 mg, 0.1 mmol/g) was placed in a polyethylene vessel equipped with a polypropylene filter for filtration and treated with ethylenediamine as earlier described. The first 6 lysines forming the presequence were coupled as Fmoc-protected and side chain protected Pfp esters (3 eq.) with the addition of Dhbt-OFI (1 eq.). The acylations were checked by the ninhydrin test performed at 800 C as described above. The Fmoc group was deprotected as described above. After finishing the presequence, the deprotected peptide-resin was reacted with 10 eq. (+)-4-methoxymandelic acid as a preactivated Hobt-ester as described above (resolved as described above, 95.8% optical purity) and the coupling was continued for 24 h. Excess reagent was removed by DMF washing (12 min, flow rate 1 ml/min). The acylation was checked by the ninhydrin test. The next amino acid according to the sequence was coupled as Fmoc protected and side chain protected preformed symmetrical anhydride as described above and the reaction was continued for 2 h. Excess reagent was then removed by DMF washing (12 min flow rate 1 ml/min). A small resin-sample was removed in order to check the coupling yield, which was estimated as described above, and found to be 66%. The synthesis was then continued by cleavage of the Fmoc group as described above.

The first alanine was coupled as a Fmoc-protected Pfp ester (3 eq.) with the addition of Dhbt-OH (1 eq.) in DMF (2 ml) for 2 h. Excess reagent was then removed by DMF washing (12 min, flow rate 1 ml/min) and the acylation was checked by the ninhydrin test performed at 80° C. as described above. The Fmoc group was then removed by treatment with 2% piperidine in DMF v/v (1 min, flow rate 1 ml/min) followed by flushing with DMF (10 sec, flow rate 10 ml/min), flowing with 0.2% Dhbt-OH in DMF (20 min, flow rate 1 ml/min) and finally washing with DMF (2×5 ml, 1 min each). The following Fmoc-protected alanine was coupled immediately as a Pfp ester (3 eq.) with the addition of 1 eq. Dhbt-OH in DMF (2 ml) for 2 h. The acylation was checked by the ninhydrin test performed as described above. The remaining amino acids according to the sequence were coupled as Fmoc-protected Pfp esters (3 eq.) with the addition of Dhbt-OH (1 eq.) in DMF (2 ml). Excess reagent was removed by DMF washing (12 min flow rate 1 ml/min) and acylations were checked by the ninhydrin test performed 80° C. as described above. The Fmoc group was deprotected as described above. After completed synthesis, the peptide-resin was washed with DMF (10 min, flow rate 1 ml/min), DCM (3×5 ml, 1 min each), diethyl ether (3×5 ml, 1 min each) and dried in vacuo.

The peptide was cleaved from the resin as described above and freeze dried from glacial acetic acid. The crude freeze dried product was analyzed by HPLC and found to be homogeneous without deletion and Fmoc-protected sequences.

Synthesis of H-Ala$_{10}$-Lys-OH (SEQ ID NO:3) Using (Glu (OtBu))6 (SEQ ID NO:36) as presequence and (+)-4 methoxymandelic acid as linker (H-Ala$_{10}$-Lys(Boc)-OCH(4-MeOPh)CO-(Glu(OtBu))$_6$—NHCH$_2$CH$_2$NH PepSyn K resin) (SEQ ID NO:35)

Dry PepSyn K (ca 500 mg) was placed in a polyethylene vessel equipped with a polypropylene filter for filtration and treated with ethylenediamine as described above. The first 6 glutamic acids forming the presequence, were coupled as Fmoc-Glu(OtBu)-Pfp esters (3 eq.) with the addition of Dhbt-OH (1 eq.). The acylations were checked by the ninhydrin test performed at 80° C. as described above. The Fmoc group was deprotected as described above. After finishing the presequence, 10 eq. (+)-4-methoxymandelic acid (resolved as described above, 95.8% optical purity) was coupled as a preactivated HObt-ester as described above. The coupling was continued for 24 h and excess reagent was then removed by DMF washing (12 min flow rate 1 ml/min). The acylation was checked by the ninhydrin test. The next amino acid according to the sequence was coupled as Fmoc protected and side chain protected preformed symmetrical anhydride as described above catalyzed by DMAP (0.1 eq.) and the reaction was continued for 2 h. Excess reagent was removed by DMF washing (12 min flow rate, 1 ml/min). A small resin-sample was removed in order to check the coupling yield, which was estimated as described above and the yield found to be 75%. The synthesis was then continued by cleavage of the Fmoc group as described above.

The first alanine was coupled as a Fmoc-protected Pfp ester (3 eq.) with the addition of Dhbt-OH (1 eq.) in DMF (2 ml) for 2 h. Excess reagent was then removed by DMF washing (12 min flow rate 1 ml/min) and the acylation was checked by the ninhydrin test performed at 80° C. as described above. The Fmoc group was then removed by treatment with 2% piperidine in DMF v/v (1 min, flow rate 1 ml/min) followed by flushing with DMF (10 sec, flow rate 10 ml/min), flowing with 0.2% Dhbt-OH in DMF (20 min, flow rate 1 ml/min) and finally washing with DMF (2×5 ml, 1 min each). The following Fmoc-protected alanine was coupled immediately as a Pfp ester (3 eq.) with the addition of 1 eq Dhbt-OH in DMF (2 ml) for 2 h. The acylation was checked by the ninhydrin test performed as described above. The remaining amino acids according to the sequence were coupled as Fmoc-protected Pfp esters (3 eq.) with the addition of Dhbt-OH (1 eq.) in DMF (2 ml). Excess reagent was removed by DMF washing (12 min flow rate 1 ml/min) and acylations were checked by the ninhydrin test performed 80° C. as described above. The Fmoc group was deprotected as described above. After completed synthesis, the peptide-resin was washed with DMF (10 min, flow rate 1 ml/min), DCM (3×5 ml, 1 min each), diethyl ether (3×5 ml, 1 min each) and dried in vacuo.

The peptide was cleaved from the resin as described above and freeze dried from glacial acetic acid. The crude freeze dried product was analyzed by HPLC and found to be homogeneous without deletion and Fmoc-protected sequences.

Results and Discussion

In the basic studies, the synthesis of H-(Ala)$_n$-(Lys)$_m$-OH (SEQ ID NO:12), where (Lys)$_m$ represent the presequence with m equal to 1, 3 and 6 was investigated. A continuous-flow version of the polyamide solid-phase method (Dryland, A. and Sheppard, R. C. (1986) J. Chem. Soc. Perkin Trans. I, 125–137.) on a fully automated peptide synthesizer developed was used as previously described (Cameron, L., Meldal, M. and Sheppard, R. C (1987), J. Chem. Soc. Chem. Commun. 270–272.) with DMF as solvent and 3 times excess of Fmoc-alanine and Fmoc-lysine(tBoc)-pfp esters, respectively and standard Fmoc-deprotection with 20% piperidine in DMF for 10 minutes. Coupling times were monitored with Dhbt-OH which is deprotonated to the yellow Dbht-O$^-$ anion when un-acylated amino groups are still present and disappearance of the yellow colour marks the end-point of the synthesis. After cleavage of the peptide from the resin with 95% aqueous TFA, the product was washed with ether and analyzed by HPLC.

In the case of synthesis of H-(Ala)n-Lys-OH on a polyamide polymerized kieselguhr matrix (PepSyn K), no problems were observed until n=5, but approximately 20–25% Fmoc-protected peptide was still present after standard deprotection with piperidine (20% piperidine in DMF) with n=6. When continuing the synthesis to n=10, a relatively complicated mixture was obtained comprising the target peptide (n=10) as well as deletion peptides corresponding to n=6, 7, 8, and 9 and deletion peptides with the Fmoc group still attached to the N-terminal where n=6, 7, 8, and 9 respectively (FIG. 2). This mixture was identified by FAB MS after HPLC separation of the single components. Failure sequences or partial deprotection with n=2–5 or incomplete deprotection of the target peptide (n=10) was not observed, thus confining the problems to a given stretch of the homo-oligopeptide chain. This type of difficult aminoacylations and incomplete deprotections can therefore be referred to as non-random in contrast to random difficulties which are due only to common steric problems. Although experimental conditions were varied, e.g. resin-type, deprotection time, solvents, addition of chaotropes, problems still persisted although heating to 50° C. had an optimal effect on incomplete Fmoc-deprotection.

Figure 4:
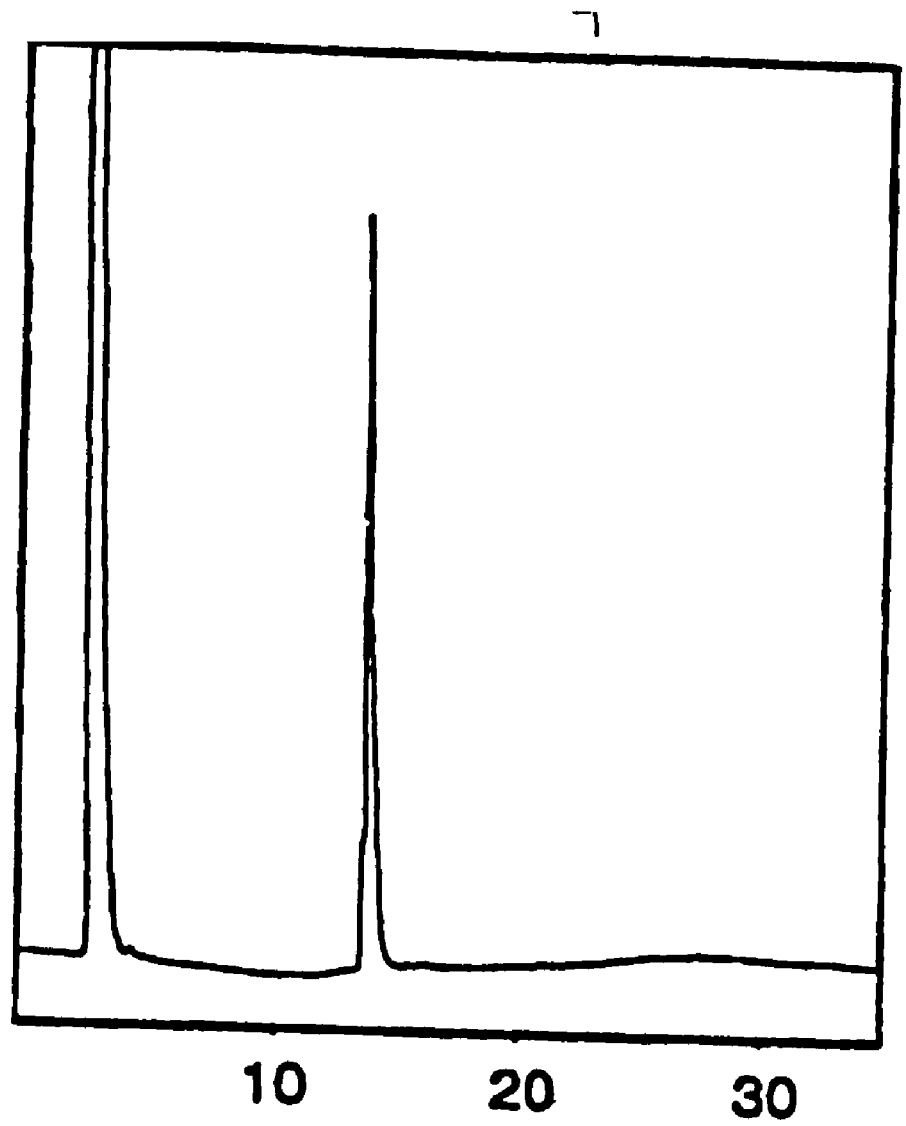
FIG. 4 is an HPLC of H-Ala$_{10}$-Lys$_3$-OH (SEQ ID NO:4) showing the target peptide. No deletion peptides were observed.
Figure 7:
FIG. 7 is an HPLC of H-Ala$_{20}$-Lys$_6$-OH (SEQ ID NO:7). No deletion peptides were observed.

In the case of m=3, it was seen from the HPLC trace shown in FIG. 4 that the synthesis may be continued to $Ala_{10}$ (SEQ ID NO:43) without detectable amounts of deletion peptides or incomplete Fmoc-deprotection. However, when continuing the synthesis to $Ala_{20}$ (SEQ ID NO:14), the chromatogram (FIG. 5) shows the presence of a small amount of deletion peptides. The results are even more striking with H-(Ala)$_n$-(Lys)$_6$-OH (SEQ ID NO:13), where products without detectable deletion peptides are obtained with both $Ala_{10}$ (SEQ ID NO:43) (FIG. 6) and $Ala_{20}$ (SEQ ID NO:14) (FIG. 7). Furthermore, coupling times are drastically reduced from up to 30 hours to standard coupling times (<2 hours) in the single steps.

Previous attempts to synthesize the H-$Ala_{20}$-OH (SEQ ID NO:14) sequence by the Boc-methodology have been made but high levels of deletion and insertion peptides were obtained (Merrifield, R. B., Singer, J. and Chait, B. T. (1988) Anal. Biochem. 174,399–414.). Clearly the presequence $Lys_6$ (SEQ ID NO:15), which under the prevailing synthesis conditions was fully protected with the tBoc-group, has a most definitive and favourable effect on the structure of the growing peptide chain eliminating the otherwise very severe synthetic problems due to incomplete deprotections and extremely slow couplings. In the case of other homo-oligo presequences, it has been observed that (Glu(tBu))$_6$ (SEQ ID NO:16), as well as the mixed sequence (Glu(tBu)Lys(tBoc))$_3$ (SEQ ID NO:17) induces a favourable structure in the poly-alanine chain affording products without deletion peptides.

In the above described cases, the peptide sequences have been obtained with a hexa lysine presequence which for certain purposes may be acceptable or even of advantage. Thus, a β-sheet forming sequence may cause severe solubility problems, but in the case of H-$Ala_{20}$(Lys)$_6$-0H (SEQ ID NO:7), the peptide turned out to be soluble in aqueous solutions while H-$Ala_{10}$-Lys-OH (SEQ ID NO:3) very rapidly precipitated from TFA solutions when diluted with water. In case of (Glu)$_6$ (SEQ ID NO:23), the solubility provided by the presequence and the multitude of carboxylic acid groups may be utilized for e.g. ELISA, where site-directed attachment to a suitably amino-group activated surface was possible because of facile activation in aqueous solution with e.g. a carbodiimide. However, it has also been considered, how the observations may be utilized for practical peptide synthesis without presence of the presequence in the final product.

Figure 10:
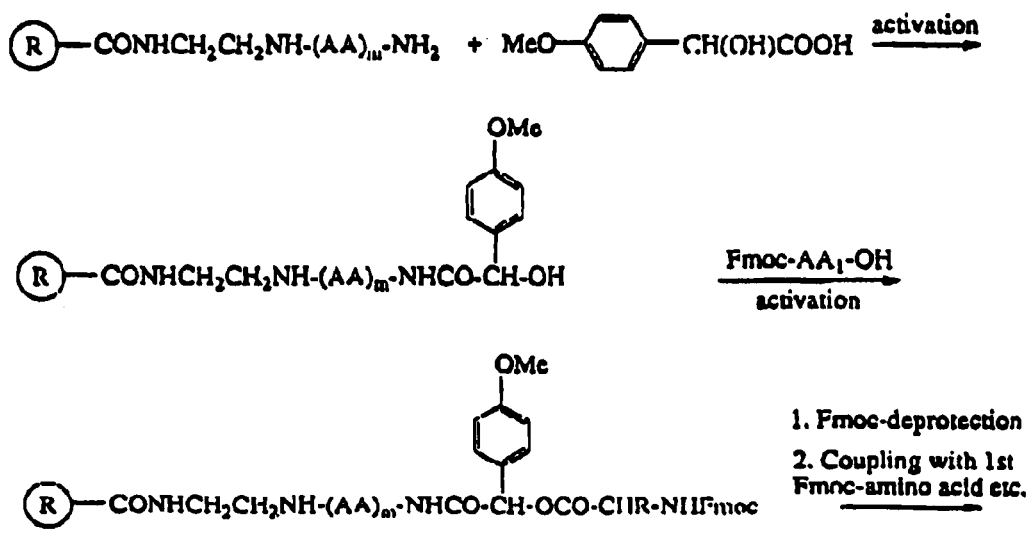
FIG. 10 shows the synthetic scheme used in a specific embodiment of the invention.

The introduction of an optically active linker between (Ala)$_n$ and (Lys)$_m$ was investigated using 4-methoxymandelic acid (MMa) as a possible candidate. This type of linker has supposedly not been used hitherto. The presence of the methoxy group was assumed to facilitate the cleavage of the target peptide from the linker by means of standard scavenger containing TFA solutions. 4-Methoxymandelic acid may be resolved in its optically active forms of which the R-configuration ((+)-configuration) was identical to L-protein amino acids. Two types of experiments have been carried out: (a) synthesis using racemic 4-methoxymandelic acid; (b) synthesis using R-4-methoxymandelic acid (R-MMa). The synthesis scheme is shown in FIG. 10 and described above.

In the first case, the sequence resin-Lys(tBoc))$_6$-MMa-Lys-$Ala_{10}$ (SEQ ID NO:25) was synthesized to give H-Lys-$Ala_{10}$-OH (SEQ ID NO:26) where the lysine group was introduced to enhance solubility in aqueous solutions for HPLC analysis. The results of the HPLC analysis are shown in FIG. 9. A much better product was achieved than for the HMPA-linker (SEQ ID NO: 24) (FIG. 8) although deletion peptides are present. In case (b) the same peptide was synthesized under identical conditions and a peptide was formed without detectable deletion peptides or incomplete Fmoc-deprotection. These results may be compared to synthesis of H-Lys-$Ala_{10}$-OH (SEQ ID NO:26) using the construct resin-MMa-Lys-$Ala_{10}$ (SEQ ID NO:27) where the presequence Lys(tBoc))$_6$ (SEQ ID NO:21) was omitted.

Syntheses of Difficult Sequences

To investigate whether SAPS is a more general phenomenon or if it is confined only to homo-oligopeptides such as the polyalanine sequence, some mixed sequences reputedly known as "difficult sequences" were investigated.

The synthesis of H-VQAAIDYING-OH (SEQ ID NO:8), Acyl Carrier Protein (ACP) 65–74, is a well known difficult synthesis and has been used as a model reaction in a number of cases (Cameron et al., (1987), J. Chem. Soc. Chem. Commun. 270–272).

Peptide Synthesis

Synthesis of Acyl Carrier Protein (ACP) 65–74, H-Val-Gln-Ala-Ala-Ile-Asp-Tyr-Ile-Asn-Gly-OH (SEQ ID NO:8) (Comparison)

500 mg Fmoc-Gly PepSyn KA resin (0.074 mmol/g) was used for synthesis according to "continuous-flow technique".

Figure 11:
FIG. 11 is an HPLC of H-VQAAIDYING-OH (SEQ ID NO:8), Acyl Carrier Protein (ACP) (65–74). The target peptide (peak 3) was accompanied with deletion peptides (peak 2 is the des-Val peptide).

The crude freeze dried product was analyzed by HPLC and found to contain the target molecule accompanied by ca. 16% of the des-Val peptide (see FIG. 11). The identity of the peptides was confirmed by MALDI TOF MS.

Synthesis of Acyl Carrier Protein (ACP) 65–74, H-Val-Gln-Ala-Ala-Ile-Asp-Tyr-Ile-Asn-Gly-Lys$_6$-OH (SEQ ID NO:9) Using the Presequence (Lys(Boc)$_6$ (SEQ ID NO:22)

500 mg Fmoc-Lys(Boc) PepSyn KA resin (0.086 mmol/g) was used for synthesis according to the "continuous-flow technique".

Figure 12:
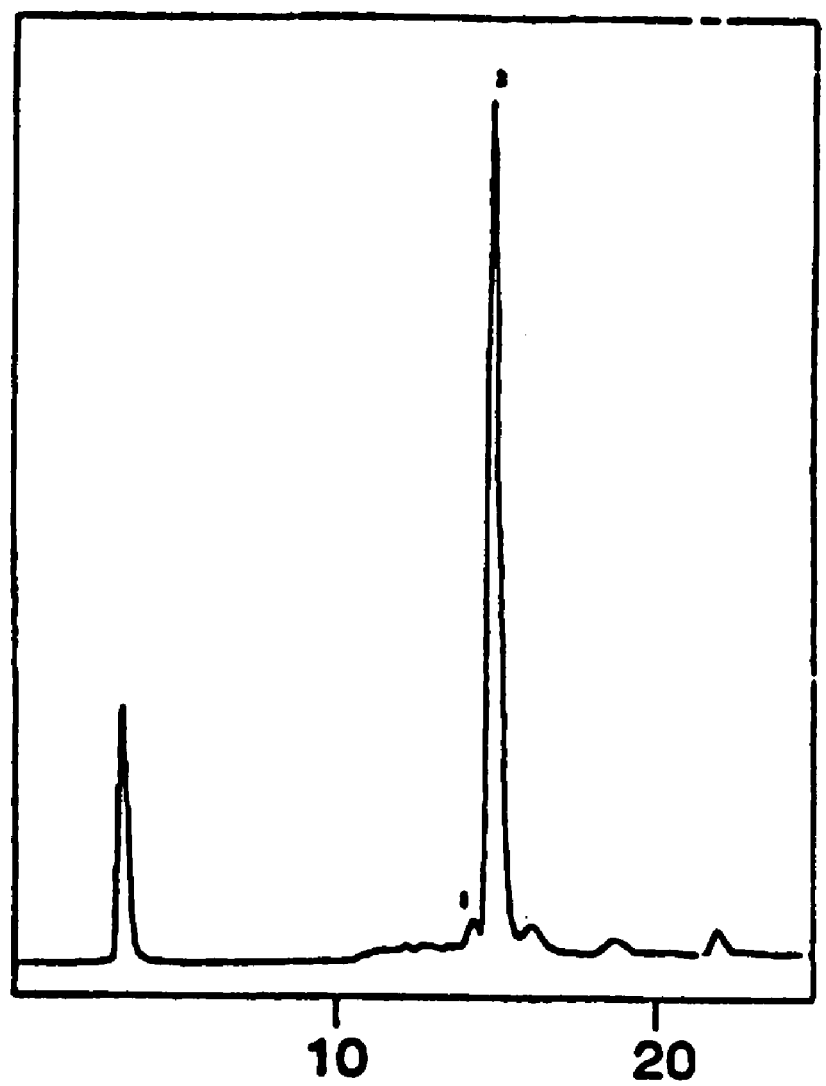
FIG. 12 is an HPLC of H-VQAAIDYING-K$_6$-OH (SEQ ID NO:9), Acyl Carrier Protein (ACP) 65–74 coupled to the Lys(Boc)$_6$ (SEQ ID NO:22) presequence with only a minor amount of desVal peptide (peak 1).

The crude freeze dried product was analyzed by HPLC and found to contain the target peptide in high purity (~95%) with a significantly reduced amount of the des-Val peptide. The identity of the peptide was confirmed by MALDI TOF MS (FIG. 12).

Synthesis of H-Val-Asn-Val-Asn-Val-Gln-Val-Gln-Val-Asp-Lys$_6$-OH (SEQ ID NO:19), Using the Presequence (Lys (Boc))$_6$ (SEQ ID NO:22)

500 mg Fmoc-Lys(Boc) PepSyn KA resin (0.086 mmol/g) was used for synthesis according to the "continuous-flow technique".

The crude freeze dried product was analyzed by HPLC and found to be better than 90% pure without deletion and Fmoc-protected sequences. Yield 100%. The identity of the peptide was confirmed by MALDI TOF MS.

Peptide-Synthesis-of Tyr-Gly-Gly-Phe-Leu-Lys$_6$-OH (SEQ ID NO:37) on NovaSyn TentaGel Dry NovaSyn TG resin (0.29 mmol/g, 250 mg) was placed in a polyethylene vessel equipped with a polypropylene filter for filtration and treated as described under "batchwise peptide synthesis on PEG-PS" until finishing the presequence Lys$_6$. The following amino acids forming the Leu-enkephalin sequence were coupled as preformed Fmoc-protected HObt esters (3 eq.) in DMF (5 ml) generated by means of DIC. Before each of the last five couplings a solution of Dhbt-OH (80 mg in 25 ml) is added to follow the disappearance of the yellow color as the coupling reaction proceeds. When the yellow color was no longer visible the couplings were interrupted by washing the resin with DMF (5×5 ml, 5 min each). The acylations were then checked by the ninhydrin test performed at 80° C. as earlier described. After completed synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin as described above and freeze dried from acetic acid. The crude freeze dried product was analyzed by HPLC and found to be homogeneous without deletion and Fmoc-protected sequences. The purity was found to be better than 98% and the identity of the peptide was confirmed by ESMS. Yield 84%.

Results and Discussion

As described above, the difficult sequence HVQAAIDY-ING-K$_6$-OH (SEQ ID NO:9) was synthesized using the presequence (Lys(tBoc))$_6$ (SEQ ID NO:21) attached at the C-terminus on a pepsyn K. The synthesis proceeded to give a product with the correct molecular weight in high purity and a significantly reduced amount of des-Val peptide.

Another difficult sequence is reported to be HVNVN-VQVQVD-OH (SEQ ID NO:18) which has been synthesized on a variety of flow resins (Rapp polymer, PEG-PS, Pepsyn K, PEGA 1900/300, PEGA 800/130 and PEGA 300/130) in all cases accompanied by considerable glutamine preview already from Val[1] except when using a PEGA 1900/300 resin (Meldal, M. (1993), Peptides 1993; Schneider, C. H. and Eberle, A. N. (Eds) 1993 ESCOM Science Publishers B, V., p. 61–62). In accordance with the invention, the synthesis of H-VNVNVQVQVDK$_6$-OH (SEQ ID NO:19) proceeded to give a product with the correct molecular weight. Deletion peptides were not detected in the spectrum.

In order to verify another important aspect of the present invention, viz. the reduced coupling times obtained by introducing a presequence at the C-terminal part of desired peptide the coupling times of the individual amino acids in the synthesis of enkephalin, H-Tyr-Gly-Gly-Phe-Leu-OH (SEQ ID NO:20), have been monitored with and without the presequence (Lys(tBoc))$_6$ (SEQ ID NO:21). These results are shown in Table 2.

TABLE 2

| | Peptide-resin | Coupling time | |
|---|---|---|---|
| Amino acid | Pre-sequence (Lys(tBoc))$_6$ (SEQ ID NO: 21) | With pre-sq. | Without pre-sq |
| Fmoc-Leu-OH | H-Lys(Boc)$_6$-HMPA-R (SEQ ID NO:22) | <2 min | — |
| Fmoc-Phe-OH | H-Leu-Lys(Boc)$_6$-HMPA-R (SEQ ID NO:38) | <5 min | <120 min |
| Fmoc-Gly-OH | H-Phe-Leu-Lys(BOC)$_6$-HMPA-R (SEQ ID NO:39) | <2 min | <60 min |
| Fmoc-Gly-OH | H-Gly-Phe-Leu-Lys(tBOc)$_6$-HMPA-R (SEQ ID NO:40) | <2 min | <60 min |
| Fmoc-Tyr-OH | H-Gly-Gly-Phe-Leu-Lys(tBoc)$_6$-HMPA-R (SEQ ID NO:41) H-Tyr-Gly-Gly-Phe-Leu-Lys(tBoc)$_6$-HMPA-R (SEQ ID NO:42) | <1 min | <40 min |

R = NovaSyn TG derivatized with the linker 4-hydroxymethyl-phenoxy acetic acid (HMPA) (Subst.: 0.29 mmol/g). Coupling times are based on the Dhbt-OH and the ninhydrin test.

The results of the measurements demonstrate that the coupling times in this otherwise uncomplicated synthesis proceeds effectively in combination with the chosen presequence.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

What is claimed is:

1. A method of synthesizing a target peptide having the following structure:

$$X-AA_1-AA_2\ldots AA_n-Y,$$

wherein,
AA is an L or D amino acid residue,
X is hydrogen or an amino protective group,
Y is OH or NH$_2$, and
n is an integer greater than about 2 and less than about 60;
said method comprising:
a. coupling a pre-sequence peptide to a support, wherein said pre-sequence peptide comprises from about 3 to about 9 amino acid residues having side chain functionalities which are, protected during the synthesis, wherein each of the amino acid residues has a propensity factor $P_\alpha > 0.57$ and a propensity factor $P_\beta \leq 1.10$,
b. coupling one or more N-α-protected amino acids to the N-terminus of the pre-sequence peptide or to a cleavable linker attached to the N-terminus of the pre-sequence peptide to form said target peptide, wherein each coupling is performed in stepwise fashion and under conditions in which each of the amino acids of the target peptide is coupled and subsequently N-α-deprotected; wherein the pre-sequence peptide reduces or eliminates propensity of the target peptide to adopt a β-sheet structure during the coupling and increases the coupling efficiency during the synthesis of the target peptide in comparison to the synthesis of the target peptide prepared under the same conditions without said pre-sequence peptide; and
c. cleaving said target peptide from said pre-sequence peptide.

2. The method of claim 1, wherein the pre-sequence peptide is enzymatically cleaved from said target peptide.

3. The method of claim 1, wherein the pre-sequence peptide comprises amino acid residues that lack propensity to adopt the β-sheet structure.

4. The method of claim 1, wherein the method further comprises removing the N-α-protective group from the target peptide before step (c).

5. The method of claim 1, wherein the method further comprises at least one of the following steps: inserting a first linker between the target peptide and the pre-sequence peptide, and inserting a second linker between the pre-sequence peptide and the support.

6. The method of claim 5, wherein step (c) further comprises cleaving the first linker, the second linker or both the first and second linkers to produce the target peptide.

7. The method of claim 1, wherein said pre-sequence peptide consists of from 5 to 7 amino acid residues.

8. The method of claim 1, wherein said pre-sequence peptide consists of a polylysine.

9. The method of claim 8, wherein said pre-sequence peptide consists of -(Lys)$_6$-.

10. The method of claim 1, wherein the yield or purity of the target peptide is increased in comparison to the synthesis of the target peptide prepared under the same conditions without said pre-sequence peptide.

* * * * *

UNITED STATES PATENT AND TRADEMARK OFFICE
CERTIFICATE OF CORRECTION

PATENT NO. : 7,176,282 B1  Page 1 of 1
APPLICATION NO. : 09/551336
DATED : February 13, 2007
INVENTOR(S) : Holm et al.

It is certified that error appears in the above-identified patent and that said Letters Patent is hereby corrected as shown below:

On the Cover Sheet, under References Cited, Under OTHER PUBLICATIONS, in "Medal et al," replace "Medal" with -- Meldal --.

Column 1,
  Line 37, replace "resin This" with -- resin. This --.
  Line 49, replace "SPPC" with -- SPPS --.

Column 2, Line 66, replace "N-αprotective" with -- N-α protective --.

Column 10,
  Line 16, in Table, "Abbreviations – continued," in "HATU," replace "hexaflurophosphate" with -- hexafluorophosphate --.
  Line 41, in Table, "Abbreviations – continued," in "TFE," replace "trifluorethanol" with -- trifluoroethanol --.

Column 11,
  Line 6, replace "pentaflorophenyl" with -- pentafluorophenyl --.
  Line 28, replace "as linker," with -- as a linker, --.

Column 12, Line 46, replace "triflouroacetic acid" with -- trifluoroacetic acid --.

Signed and Sealed this

Nineteenth Day of August, 2008

JON W. DUDAS
*Director of the United States Patent and Trademark Office*

SEQUENCE LISTING

<160> NUMBER OF SEQ ID NOS: 43

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: synthetic peptide
<223> OTHER INFORMATION: this peptide may also encompass a deletion -continued peptide of 2-9 Ala

<400> SEQUENCE: 1

Ala Ala Ala Ala Ala Ala Ala Ala Ala Ala Lys
 1               5                  10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Ala Ala Ala Ala Ala Ala Ala
 1               5

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Ala Ala Ala Ala Ala Ala Ala Ala Ala Ala Lys
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Ala Ala Ala Ala Ala Ala Ala Ala Ala Ala Lys Lys Lys
 1               5                  10

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Ala Ala Ala Ala Ala Ala Ala Ala Ala Ala Ala Ala Ala Ala Ala
 1               5                  10                  15

Ala Ala Ala Ala Lys Lys Lys
            20

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

Ala Ala Ala Ala Ala Ala Ala Ala Ala Ala Lys Lys Lys Lys Lys Lys
 1               5                  10                  15

```
<210> SEQ ID NO 7
<211> LENGTH: 26
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Ala Ala Ala Ala Ala Ala Ala Ala Ala Ala Ala Ala Ala Ala Ala
 1               5                  10                  15

Ala Ala Ala Ala Lys Lys Lys Lys Lys Lys
            20                  25

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: acyl
      carrier protein (65-74)

<400> SEQUENCE: 8

Val Gln Ala Ala Ile Asp Tyr Ile Asn Gly
 1               5                  10

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: acyl
      carrier protein (65-74)-(Lys)6

<400> SEQUENCE: 9

Val Gln Ala Ala Ile Asp Tyr Ile Asn Gly Lys Lys Lys Lys Lys Lys
 1               5                  10                  15

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (11)
<223> OTHER INFORMATION: Lys(tBoc)-HMPA
<221> NAME/KEY: MOD_RES
<222> LOCATION: (12)..(17)
<223> OTHER INFORMATION: Lys(tBoc)

<400> SEQUENCE: 10

Ala Ala Ala Ala Ala Ala Ala Ala Ala Ala Lys Lys Lys Lys Lys Lys
 1               5                  10                  15

Lys

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (11)
<223> OTHER INFORMATION: Lys-MMa
```

```
<221> NAME/KEY: MOD_RES
<222> LOCATION: (12)..(17)
<223> OTHER INFORMATION: Lys(tBoc)

<400> SEQUENCE: 11

Ala Ala Ala Ala Ala Ala Ala Ala Ala Ala Lys Lys Lys Lys Lys Lys
 1               5                  10                  15

Lys

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence: synthetic
      peptide
<223> OTHER INFORMATION: this peptide may also encompass a deletion
      peptide of 10 Ala
<223> OTHER INFORMATION: this peptide may also encompass a deletion
      peptide of 1 or 3 Lys

<400> SEQUENCE: 12

Ala Ala Ala Ala Ala Ala Ala Ala Ala Ala Ala Ala Ala Ala Ala Ala
 1               5                  10                  15

Ala Ala Ala Ala Lys Lys Lys Lys Lys Lys
            20                  25

<210> SEQ ID NO 13
<211> LENGTH: 26
<212> TYPE: PRT
<213> ORGANISM: Artificial Sequence
<220> FEATURE:
<223> OTHER INFORMATION: Description of Artificial Sequence: synthetic
      peptide
<223> OTHER INFORMATION: this peptide may also encompass a deletion
      peptide of 10 Ala

<400> SEQUENCE: 13

Ala Ala Ala Ala Ala Ala Ala Ala Ala Ala Ala Ala Ala Ala Ala Ala
 1               5                  10                  15

Ala Ala Ala Ala Lys Lys Lys Lys Lys Lys
            20                  25

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Ala Ala Ala Ala Ala Ala Ala Ala Ala Ala Ala Ala Ala Ala Ala Ala
 1               5                  10                  15

Ala Ala Ala Ala
            20

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 15
```

```
Lys Lys Lys Lys Lys Lys
  1               5
```

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (1)..(6)
<223> OTHER INFORMATION: Glu(tBu)

<400> SEQUENCE: 16

```
Glu Glu Glu Glu Glu Glu
  1               5
```

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (1)..(2)
<223> OTHER INFORMATION: Glu(tBu)Lys(tBoc)
<221> NAME/KEY: MOD_RES
<222> LOCATION: (3)..(4)
<223> OTHER INFORMATION: Glu(tBu)Lys(tBoc)
<221> NAME/KEY: MOD_RES
<222> LOCATION: (5)..(6)
<223> OTHER INFORMATION: Glu(tBu)Lys(tBoc)

<400> SEQUENCE: 17

```
Glu Lys Glu Lys Glu Lys
  1               5
```

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 18

```
Val Asn Val Asn Val Gln Val Gln Val Asp
  1               5                  10
```

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 19

```
Val Asn Val Asn Val Gln Val Gln Val Asp Lys Lys Lys Lys Lys Lys
  1               5                  10                  15
```

<210> SEQ ID NO 20
<211> LENGTH: 5
<212> TYPE: PRT
<213> ORGANISM: Homo sapiens
<220> FEATURE:
<223> OTHER INFORMATION: Enkephalin

```
<400> SEQUENCE: 20

Tyr Gly Gly Phe Leu
  1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (1)..(6)
<223> OTHER INFORMATION: Lys(tBoc)

<400> SEQUENCE: 21

Lys Lys Lys Lys Lys Lys
  1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (1)..(6)
<223> OTHER INFORMATION: Lys(tBoc)

<400> SEQUENCE: 22

Lys Lys Lys Lys Lys Lys
  1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 23

Glu Glu Glu Glu Glu Glu
  1               5

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (1)..(6)
<223> OTHER INFORMATION: Lys(tBoc)
<221> NAME/KEY: MOD_RES
<222> LOCATION: (7)
<223> OTHER INFORMATION: HMPA-Lys(tBoc)

<400> SEQUENCE: 24

Lys Lys Lys Lys Lys Lys Lys Ala Ala Ala Ala Ala Ala Ala Ala
  1               5                  10                  15

Ala

<210> SEQ ID NO 25
<211> LENGTH: 17
<212> TYPE: PRT
```

```
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (1)..(6)
<223> OTHER INFORMATION: Lys(tBoc)
<221> NAME/KEY: MOD_RES
<222> LOCATION: (7)
<223> OTHER INFORMATION: MMa-Lys

<400> SEQUENCE: 25

Lys Lys Lys Lys Lys Lys Lys Ala Ala Ala Ala Ala Ala Ala Ala
 1               5                  10                  15

Ala

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 26

Lys Ala Ala Ala Ala Ala Ala Ala Ala Ala Ala
 1               5                  10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (1)
<223> OTHER INFORMATION: MMa-Lys

<400> SEQUENCE: 27

Lys Ala Ala Ala Ala Ala Ala Ala Ala Ala Ala
 1               5                  10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (11)..(13)
<223> OTHER INFORMATION: Lys(Boc)

<400> SEQUENCE: 28

Ala Ala Ala Ala Ala Ala Ala Ala Ala Ala Lys Lys Lys
 1               5                  10

<210> SEQ ID NO 29
<211> LENGTH: 27
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 29

Ala Ala Ala Ala Ala Ala Ala Ala Ala Ala Ala Ala Ala Ala Ala
 1               5                  10                  15
```

```
Ala Ala Ala Ala Lys Gly Lys Gly Lys Gly Lys
            20                  25
```

<210> SEQ ID NO 30
<211> LENGTH: 23
<212> TYPE: PRT
<213> ORGANISM: Artificial Sequence
<220> FEATURE:
<223> OTHER INFORMATION: Description of Artificial Sequence: synthetic
      peptide
<223> OTHER INFORMATION: this peptide may also encompass a deletion
      peptide of 16-19 Ala

<400> SEQUENCE: 30

```
Ala Ala Ala Ala Ala Ala Ala Ala Ala Ala Ala Ala Ala Ala Ala
  1               5                  10                  15

Ala Ala Ala Ala Lys Lys Lys
            20
```

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (11)
<223> OTHER INFORMATION: Lys(Boc)-OCH2-HMPA
<221> NAME/KEY: MOD_RES
<222> LOCATION: (12)..(17)
<223> OTHER INFORMATION: Lys(Boc)

<400> SEQUENCE: 31

```
Ala Ala Ala Ala Ala Ala Ala Ala Ala Ala Lys Lys Lys Lys Lys Lys
  1               5                  10                  15

Lys
```

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (11)
<223> OTHER INFORMATION: Lys(Boc)-OCH-MMa

<400> SEQUENCE: 32

```
Ala Ala Ala Ala Ala Ala Ala Ala Ala Ala Lys
  1               5                  10
```

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (11)
<223> OTHER INFORMATION: Lys(Boc)-OCH-MMa
<221> NAME/KEY: MOD_RES
<222> LOCATION: (12)..(17)
<223> OTHER INFORMATION: Lys(Boc)

<400> SEQUENCE: 33

Ala Ala Ala Ala Ala Ala Ala Ala Ala Ala Lys Lys Lys Lys Lys
1               5                   10                  15

Lys

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: synthetic
      peptide
<223> OTHER INFORMATION: this peptide may also encompass a deletion
      peptide of 6-9 Ala

<400> SEQUENCE: 34

Ala Ala Ala Ala Ala Ala Ala Ala Ala Ala Lys
1               5                   10

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (11)
<223> OTHER INFORMATION: Lys(Boc)-OCH-MMa-CO
<221> NAME/KEY: MOD_RES
<222> LOCATION: (12)..(17)
<223> OTHER INFORMATION: Glu(OtBu)

<400> SEQUENCE: 35

Ala Ala Ala Ala Ala Ala Ala Ala Ala Ala Lys Glu Glu Glu Glu Glu
1               5                   10                  15

Glu

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (1)..(6)
<223> OTHER INFORMATION: Glu(OtBu)

<400> SEQUENCE: 36

Glu Glu Glu Glu Glu Glu
1               5

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 37

Tyr Gly Gly Phe Leu Lys Lys Lys Lys Lys Lys
1               5                   10

<210> SEQ ID NO 38
<211> LENGTH: 7
<212> TYPE: PRT
<213> ORGANISM: Artificial Sequence

```
<220> FEATURE:
<223> OTHER INFORMATION: Description of Artificial Sequence: synthetic
      peptide
<221> NAME/KEY: MOD_RES
<222> LOCATION: (2)..(7)
<223> OTHER INFORMATION: Lys(Boc)

<400> SEQUENCE: 38

Leu Lys Lys Lys Lys Lys Lys
 1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (3)..(8)
<223> OTHER INFORMATION: Lys(Boc)

<400> SEQUENCE: 39

Phe Leu Lys Lys Lys Lys Lys Lys
 1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (4)..(9)
<223> OTHER INFORMATION: Lys(tBoc)

<400> SEQUENCE: 40

Gly Phe Leu Lys Lys Lys Lys Lys Lys
 1               5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (5)..(10)
<223> OTHER INFORMATION: Lys(tBoc)

<400> SEQUENCE: 41

Gly Gly Phe Leu Lys Lys Lys Lys Lys Lys
 1               5                  10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (6)..(11)
<223> OTHER INFORMATION: Lys(tBoc)

<400> SEQUENCE: 42

Tyr Gly Gly Phe Leu Lys Lys Lys Lys Lys Lys
 1               5                  10
```

```
<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 43

Ala Ala Ala Ala Ala Ala Ala Ala Ala Ala
 1               5                  10
```